(12) United States Patent
Potter et al.

(10) Patent No.: US 7,112,698 B2
(45) Date of Patent: Sep. 26, 2006

(54) 4-(C2-6ALKOXY)-SUBSTITUTED CHALCONES AS THERAPEUTIC AGENTS

(75) Inventors: Gerard Andrew Potter, Leicester (GB); Taeeba Ijaz, Leicester (GB)

(73) Assignee: Spear Therapeutics Limited, (GB)

( * ) Notice: Subject to any disclaimer, the term of this patent is extended or adjusted under 35 U.S.C. 154(b) by 0 days.

(21) Appl. No.: 10/491,614

(22) PCT Filed: Sep. 30, 2002

(86) PCT No.: PCT/GB02/04462

§ 371 (c)(1),
(2), (4) Date: Apr. 2, 2004

(87) PCT Pub. No.: WO03/029176

PCT Pub. Date: Apr. 10, 2003

(65) Prior Publication Data

US 2004/0259957 A1   Dec. 23, 2004

(30) Foreign Application Priority Data

Oct. 3, 2001 (GB) ................................ 0123780.9

(51) Int. Cl.
*C07C 49/76* (2006.01)
*A61K 31/12* (2006.01)
(52) U.S. Cl. ...................... 568/335; 568/337; 568/338; 514/685; 514/689
(58) Field of Classification Search ................ 568/338, 568/337; 514/685, 689
See application file for complete search history.

(56) References Cited

U.S. PATENT DOCUMENTS

| | | | |
|---|---|---|---|
| 4,279,930 A | 7/1981 | Hall et al. | 424/331 |
| 4,867,964 A * | 9/1989 | Forestier et al. | 424/47 |
| 5,430,062 A | 7/1995 | Cushman et al. | 514/646 |
| 5,691,373 A | 11/1997 | Berryman et al. | 514/464 |
| 6,214,886 B1 | 4/2001 | Potter et al. | 514/688 |
| 6,787,672 B1 * | 9/2004 | Potter et al. | 568/327 |

FOREIGN PATENT DOCUMENTS

| | | |
|---|---|---|
| GB | 2 198 945 | 6/1988 |
| JP | 61-076433 A | 4/1986 |
| JP | 02-142717 A | 5/1990 |
| JP | 05-246932 A | 9/1993 |
| JP | 08-188546 A | 7/1996 |
| WO | WO 95/05376 | 2/1995 |
| WO | WO 97/12246 | 4/1997 |
| WO | WO 99/00114 | 1/1999 |
| WO | WO 99/40056 | 8/1999 |
| WO | WO 01/46110 | 6/2001 |
| WO | WO 01/72680 | 10/2001 |

OTHER PUBLICATIONS

Geismann et al. Flavonones and related compounds. V. The oxidation of 2'-hydroxychalcones with alkaline hydrogen peroxide. Journal of the American Chemical Society; (1948), vol. 70, p. 1686-1689.*

Barrie, S.E., et al., 1989, "Inhibition of 17-hydroxylase/C17-C20 Lyase by Bifluranol and Its Analogues," *J. Steroid Biochem.*, vol. 33, No. 6, pp. 1191-1195.

Carmichael, J., et al., 1987, "Evaluation of a Tetrazolium-based Semiautomated Colorimetric Assay: Assessment of Chemosensitivity Testing," *Cancer Research*, vol. 47, p. 936-942.

de Wet, H., et al., 2001, "Sequence Requirements of the ATP-Binding Site within the C-Terminal Nucleotide-Binding Domain of Mouse P-Glycoprotein: Structure-Activity Relationships for Flavonoid Binding," *Biochemistry*, vol. 40, 10382-10391.

Ducki, S., et al., 1998, "Potent Antimitotic and Cell growth Inhibitory Properties of Substituted Chalcones," *BioMed. Chem. Lett.*, vol. 8, pp. 1051-1056.

Hsieh, H-K et al., 2000, "Synthesis and Anti-Inflammatory Effect of Chalcones," *Journal of Pharmacy and Pharmacology*, vol. 52, No. 2, pp. 163-171.

(Continued)

*Primary Examiner*—Sikarl A. Witherspoon
(74) *Attorney, Agent, or Firm*—Ivor R. Elrifi; Mintz, Levin, Cohn, Ferris, Glovsky and Popeo, P.C.

(57) ABSTRACT

The present invention pertains to compounds of the following formula: (1) wherein: $R^{ALK}$ is primary or secondary aliphatic saturated $C_{2-6}$alkyl; each of $R^{B2}$, $R^{B3}$, $R^{B4}$, and $R^{B5}$ is independently —H, —OH, or —OMe; each of $R^1$ and $R^2$ is independently: —H, optionally substituted $C_{1-4}$alkyl, or optionally substituted $C_{5-20}$aryl; $R^{A3}$ is —H, —OH, —OC(=O)$R^E$, —OS(=O)$_2$OH, or —OP(=O)(OH)$_2$; $R^E$ is: —H, optionally substituted $C_{1-6}$alkyl, optionally substituted $C_{3-20}$heterocyclyl, or optionally substituted $C_{5-20}$aryl; or a pharmaceutically acceptable salt, solvate, amide, ester, ether, chemically protected form, or prodrug thereof. The present invention also pertains to pharmaceutical compositions comprising such compounds, and the use of such compounds and compositions, both in vitro and in vivo, for both diagnosis and treatment of, for example, proliferative conditions, such as cancer, and inflammatory conditions

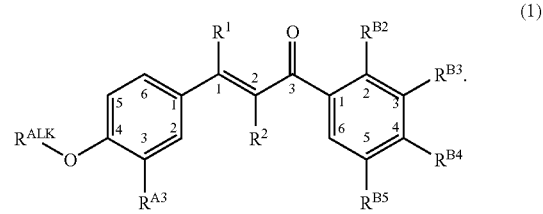

(1)

56 Claims, 1 Drawing Sheet

OTHER PUBLICATIONS

Iwata Susumu et al., 1995, "Antitumorigenic Activities of Chalcones. I. Inhibitory Effects of Chalcone Derivatives on 32P-Incorporation into Phospholipids of HeLa Cells Promoted by 12-O-Tetradecanoyl-phorbol 13-acetate (TPA)," *Biological & Pharmaceutical Bulletin(of Japan)*, vol. 18, No. 12, pp. 1710-1713.

Mosmann, T., 1983, "Rapid Colorimetric Assay for Cellular Growth and Survival: Application to Proliferation and Cytotoxicity Assays," *Journal of Immunological Methods*, vol. 65, pp. 55-63.

Murray, G. I., et al., 1997, "Tumour-specific Expression of Cytochrome P450 CYP1B1," *Cancer Research*, vol. 57, pp. 3026-3031.

Parmar, V.S., et al., 1997, "Anti-Invasive Activity of Alkaloids and Polyphenolics in Vitro," *Bioorganic & Medicinal Chemistry*, vol. 5, No. 8, pp. 1609-1619.

Pettit, G.R., et al., 1995, "Antineoplastic agents 322. Synthesis of Combretastatin A-4 Prodrugs," *Anticancer Drug Design*, vol. 10, pp. 299-309.

Shibata, S., 1994, "Anti-Tumorigenic Chalcones," *Stem Cells*, vol. 12, pp. 44-52.

Sogawa et al., 1993, "3,4-Dihydroxychalcones as Potent 5-Lipoxygenase and Cyclooxygenase Inhibitors," *Journal of Medicinal Chemistry*, vol. 36, No. 24, pp. 3904-3909.

Spink, D.C., et al., 1994, "The Effects of 2,3,7,8-Tetrachlorodibenzo-p-dioxin on Estrogen Metabolism in MCF-7 Breast Cancer Cells: Evidence for Induction of a Novel 17β-Estradiol 4-hydroxylase," *J. Steroid Biochem. Mol. Biol.*, vol. 51, No. 5/6, pp. 251-258.

Sutter, T.R., et al, 1994, "Complete cDNA sequence of a human dioxin-inducible mRNA identifies a new gene subfamily of cytochrome P450 that maps onto chromosome 2," *J. Biol. Chem.*, vol. 269, No. 18, pp. 13092-13099.

Tanaka et al., 2001, "Influence of Natural and Synthesis Compounds on Cell Surface Expression of Cell Adhesion Molecules ICAM-1 and VCAM-1," *Planta Medica*, vol. 67, No. 2, pp. 108-113.

Yamashita, D.S., et al, 1994, "Design, Synthesis and Evaluation of Dual Domain FKBP Ligands," *Bioorg. Med. Chem. Lett.*, vol. 4, No. 2, pp. 325-328.

* cited by examiner

4-(C2-6ALKOXY)-SUBSTITUTED CHALCONES AS THERAPEUTIC AGENTS

This application is the U.S. national phase of international application PCT/GB02/04462 filed 30 Sep. 2002 which designated the U.S. and claims benefit of GB 0123780.9, dated 3 Oct. 2001, the entire content of which is hereby incorporated by reference.

RELATED APPLICATION

This application is related to (and where permitted by law, claims priority to) United Kingdom patent application number GB 0123780.9 filed 3 Oct. 2001, the contents of which are incorporated herein by reference in their entirety.

TECHNICAL FIELD

This invention pertains to substituted chalcones, specifically substituted 1-(4-$C_{2-6}$alkoxyphenyl)-3-phenyl-prop-1-en-3-ones, which have therapeutic application, for example, as potent antiproliferative agents and antiinflammatory agents. The present invention also pertains to pharmaceutical compositions comprising such compounds, and the use of such compounds and compositions, both in vitro and in vivo, for both diagnosis and treatment of, for example, proliferative conditions, such as cancer, and inflammatory conditions.

BACKGROUND

Many clinically successful anticancer drugs are themselves either natural products or have been developed from naturally occurring lead compounds. Great interest is currently being paid to drugs isolated from natural resources which have already been used as a medicine. The dried whole plant of *Scutellaria barbata* D. Don (Labiatae) is used in Traditional Chinese Medicine as an anti-inflammatory, an antitumour agent, and a diuretic. The α,β-unsaturated ketone, (E)-1-(4'-hydroxyphenyl)but-1-en-3-one has been isolated from this plant and found to have moderate antitumour activity (IC50 of 60 µM for K562).

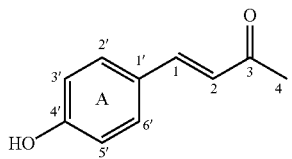

Various analogues of this compounds have been examined for antitumour activity, including one class of analogs, chalcones.

Chalcone, also known as chalkone, benzylideneacetophenone, benzalacetophenone, and phenyl styryl ketone, is 1,3-diphenyl-2-propen-1-one, and has the following structure:

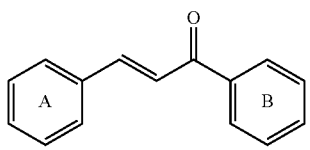

A number of substituted chalcones have been prepared, with one or more substituents on the styryl phenyl group (left, A), the acyl phenyl group (right, B), and/or the double bond carbon atoms.

A number of substituted chalcones with apparent biological activity have been reported.

Hall et al., 1981, describe a number of substituted chalcones which were alleged to have anti-inflammatory properties. The recited compounds are shown below (see Example 10, therein) (substituent is H unless otherwise specified): 1 (X=OH, Z=OH, L=OH), 2 (X=OH, Y=OH, Z=OH, L=OMe), 3 (Y=OH, L=NMe$_2$), 4 (Y=OH, L=Cl), 5 (Y=OH, K=OEt, L=OH), 6 (Y=OH, K=C$_6$H$_5$F), 7 (Y=OH, L=OH), 8 (Y=OMe, K=OMe), 9 (Y=OH, J=F), and 10 (Y=OMe, L=OH).

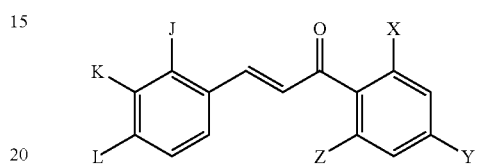

Eda Shoei et al., 1986, describe several substituted chalcones which were reported to have anti-allergic activity. Compounds 1 (X=H, Y=H), 2 (X=H, Y=H), 3 (X=OH, Y=H), 4 (X=OMe, Y=H), 5 (X=OMe, Y=OMe), 6 (X=NO$_2$, Y=H), 7 (X=NH$_2$, Y=H), (see Table 1, therein) are shown below.

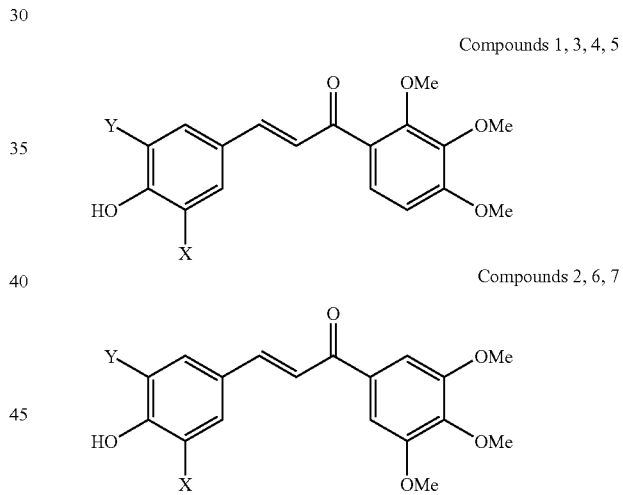

Berryman et al., 1995, 1997, describe a number of substituted chalcones which are intermediates used in the preparation of certain furanone and thiofuranone compounds reported to have activity as endothelin I antagonists.

Some of the chalcone intermediates have a 3,4-methylenedioxy group on the A-ring, as shown in the core structure below. See, e.g., in Berryman et al., 1995, Examples 36, 155, 187, 191, 195, 200, 201, 205, 209, 213, 217, 224, 232, 238, 242, 246, 263, 268, 280, 287, 288, 289, 298, 326, 345, 352, 353, 354, 355, 357, 366, 367, 368, 369, 370, 371, 378, 380, 387, 405, and 406; and additionally, in Berryman et al., 1997, Examples 421, 435, and 446. Various B-ring substituents are illustrated, including: 4-hydroxy; 2-methoxy; 3-methoxy; 4-methoxy; 2-allyloxy-4-methoxy; 4-isopropoxy; 2,4-dimethoxy; 3,4-dimethoxy; 3,4-methylenedioxy; 3,4-methylenedioxy-5-methoxy; and 3,4-ethylenedioxy.

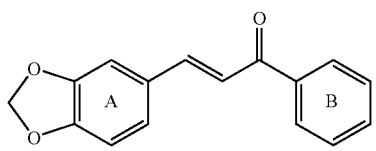

Although many of the chalcone intermediates have an A-ring substituent which is 4-methoxy, one (Example 1, page 55, in Berryman et al., 1995) has a 4-($C_{2-6}$alkoxy) substituent, specifically, a 4-isopropoxy substituent, as shown below.

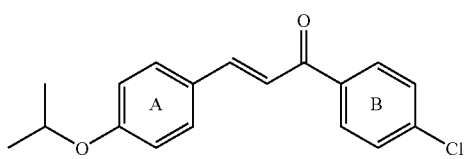

Ikeda Shunichi et al., 1996, describe several substituted chalcones reported to be active as antitumour agents. Compounds 1 (X=H) (also referred to herein as DMU-103), 2 (X=Me), and 3 (X=Et) (see Table 1, therein) are shown below.

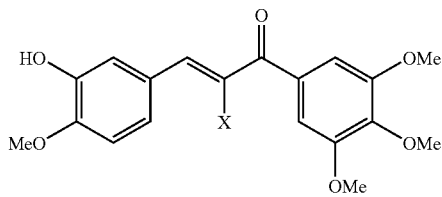

Compounds 1, 2, 3

Ducki et al., 1998, describe several substituted chalcones which were screened for cytotoxic activity against the human K562 human leukemia cell line. Compounds 2a–d (X=H) and 5a–d (X=Me) (see Table 3, therein) are shown below. The X=Me compounds were found to be much more active against K562 cells than the X=H compounds (see Table 3 therein). Compound 2b is also referred to herein as DMU-135.

Compounds 2a/5a

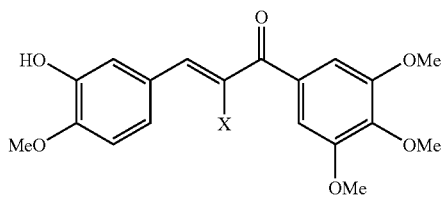

Compounds 2b/5b

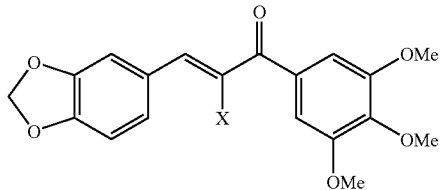

Compounds 2c/5c

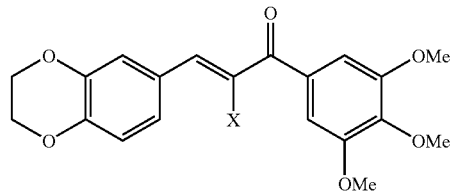

Compounds 2d/5d

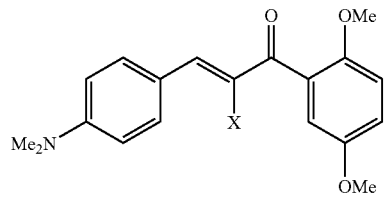

Kharazmi et al., 1999, describe a large number of substituted chalcones alleged to be suitable for the treatment of, inter alia, inflammatory conditions and neoplasias. See, e.g., Example 1 (pages 71–94) therein; the ring numbering scheme, shown below, is illustrated at page 132 therein. None of the compounds have a 4-($C_{2-6}$alkoxy) substituent or a 3,4-methylenedioxy substituent (using their numbering scheme).

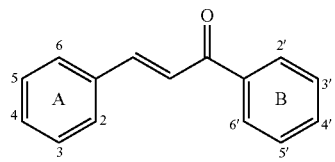

Potter et al., 1999, 2001 a, describe several 3,4,5-trimethoxy chalcones which were shown to inhibit preferentially the growth of cells expressing cytochrome P450 enzyme CYP1B1 as compared to cells which do not. Compounds VI (X=OMe, Y=H, Z=H, cis), VII (X=OMe, Y=H, Z=H, trans), VIII (X=OH, Y=H, Z=H), IX (X=OMe, Y=OMe, Z=H), XI (X=OMe, Y=H, Z=Me) are shown below. Compound VII was reported to be 200-fold more cytotoxic to the cell line expressing CYP1B1 than to the parental cell line not expressing this enzyme.

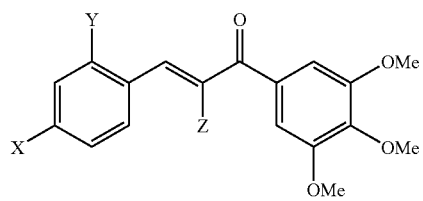

Compounds VI, VII, VIII, IX, and XI

Potter et al., 2001b, describes certain substituted 1-(4-methoxyphenyl)-3-(3,5-dimethoxyphenyl)prop-1-en-3one of the following general formula, which have therapeutic application, and which are potent antiproliferative agents and antiinflammatory agents.

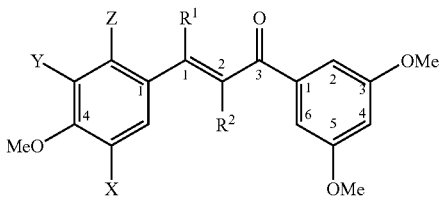

Cushman et al., 1995, describes various stilbene derviatives, which are reported to possess utility as anticancer agents.

There is a great need for additional antiproliferative agents which offer one or more of the following benefits:

(a) improved activity.
(b) improved selectivity (e.g., against tumour cells versus normal cells).
(c) low cytotoxicity as a prodrug, but yields an active drug in vivo;
(d) complement the activity of other treatments (e.g., chemotherapeutic agents);
(e) reduced intensity of undesired side-effects;
(f) fewer undesired side-effects;
(g) simpler methods of administration;
(h) reduction in required dosage amounts;
(i) reduction in required frequency of administration;
(j) increased ease of synthesis, purification, handling, storage, etc.;
(k) reduced cost of synthesis, purification, handling, storage, etc.

Thus, one aim of the present invention is the provision of compounds which are potent antiproliferative agents, e.g., anti-cancer agents, which offer one or more of the above benefits.

The inventors have discovered that certain sub-classes of substituted chalcones, described herein, offer one or more of the above benefits, and additionally are surprisingly and unexpectedly more active than corresponding known analogues.

SUMMARY OF THE INVENTION

One aspect of the invention pertains to active compounds, as described herein, which treat a proliferative condition, such as cancer.

Another aspect of the present invention pertains to a composition comprising a compound as described herein and a pharmaceutically acceptable carrier.

Another aspect of the present invention pertains to methods of regulating (e.g., inhibiting) cell proliferation, comprising contacting a cell with an effective amount of an active compound, as described herein, whether in vitro or in vivo.

Another aspect of the present invention pertains to methods of treating a proliferative condition in a subject comprising administering to said subject a therapeutically-effective amount of an active compound, as described herein. In one preferred embodiment, the proliferative condition is cancer.

Another aspect of the present invention pertains to an active compound, as described herein, for use in a method of treatment of the human or animal body by therapy.

Another aspect of the present invention pertains to an active compound, as described herein, for use in a method of treatment of a proliferative condition of the human or animal body by therapy.

Another aspect of the present invention pertains to an active compound, as described herein, for use in a method of treatment of cancer of the human or animal body by therapy.

Another aspect of the present invention pertains to an active compound, as described herein, for use in a method of treatment of an inflammatory condition of the human or animal body by therapy.

Another aspect of the present invention pertains to use of an active compound, as described herein, for the manufacture of a medicament for use in the treatment of a proliferative condition.

Another aspect of the present invention pertains to use of an active compound, as described herein, for the manufacture of a medicament for use in the treatment of cancer.

Another aspect of the present invention pertains to use of an active compound, as described herein, for the manufacture of a medicament for use in the treatment of an inflammatory condition. In one preferred embodiment, the inflammatory condition is rheumatoid arthritis, rheumatic fever, osteoarthritis, inflammatory bowel disease, psoriasis, or bronchial asthma.

In one embodiment, the proliferative condition is characterised by cells which express CYP1B1.

In one embodiment, the proliferative condition is characterised by cells which express CYP1B1, where the corresponding normal cells do not express CYP1B1.

Another aspect of the present invention pertains to a compound as described herein, wherein $R^{43}$ is —H. for use in a method of diagnosis of the human or animal body. In one preferred embodiment, the diagnosis is for the presence of tumour cells expressing the CYP1B1 enzyme.

Another aspect of the present invention pertains to the use of a compound as described herein, wherein $R^{43}$ is —H, for the presence of cells (e.g., tumour cells) expressing the CYP1B1 enzyme.

Another aspect of the present invention pertains to a method of diagnosis of a subject for the presence of cells (e.g., tumour cells) expressing the CYP1B1 enzyme, comprising:

(a) administering to the patient a compound as described herein, wherein $R^{43}$ is —H;
(b) determining the amount of the corresponding hydroxylated metabolite, wherein $R^{43}$ is —OH, which is subsequently produced; and,
(c) correlating the amount with the presence or absence of the cells (e.g., tumour cells) in the patient.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

Figure 1:
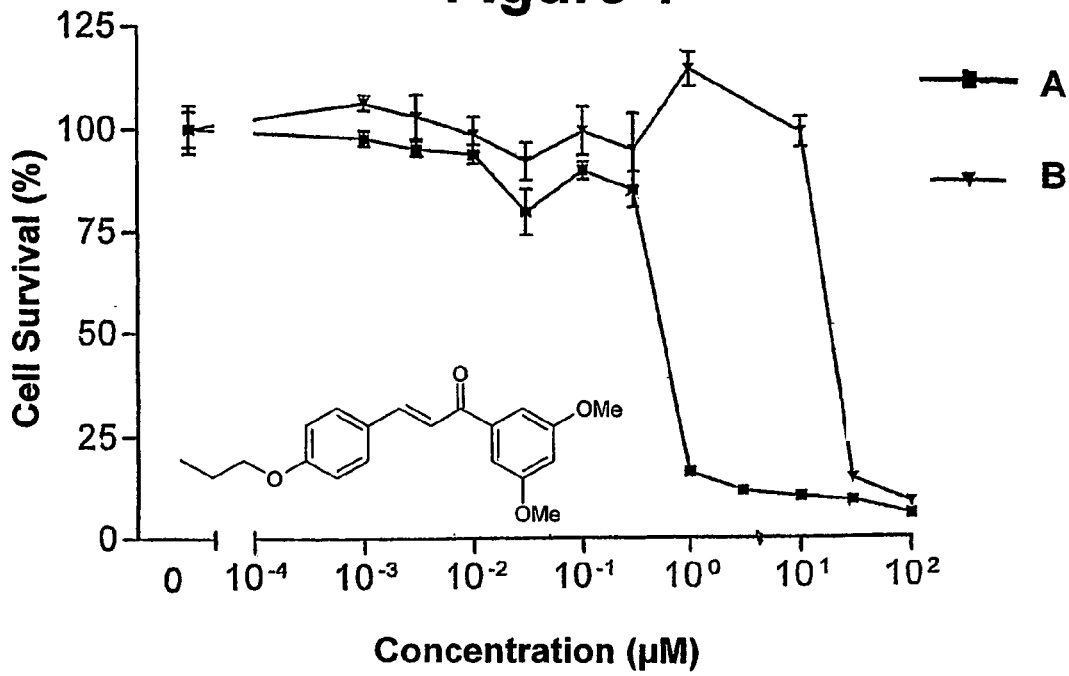
FIG. 1 is a graph of cell survivial (%) versus concentration (μM) of compound DMU-175, for (A) the TCDD-induced MCF-7 cell line (■) and (B) the MCF-7 cell line (▼).

One aspect of the present invention pertains to compounds of the following formula:

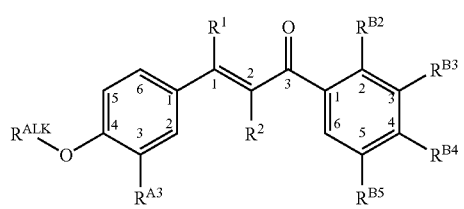

wherein:
R$^{ALK}$ is primary or secondary aliphatic saturated C$_{2-6}$alkyl;
each of R$^{B2}$, R$^{B3}$, R$^{B4}$, and R$^{B5}$ is independently —H, —OH, or —OMe;
each of R$^1$ and R$^2$ is independently —H, optionally substituted C$_{1-4}$alkyl, or optionally substituted C$_{5-20}$aryl;
R$^{A3}$ is —H, —OH, —OC(=O)R$^E$, —OS(=O)$_2$OH, or —OP(=O)(OH)$_2$;
R$^E$ is —H, optionally substituted C$_{1-6}$alkyl, optionally substituted C$_{3-20}$heterocyclyl, or optionally substituted C$_{5-20}$aryl;

and pharmaceutically acceptable salts, solvates, amides, esters, ethers, chemically protected forms, and prodrugs thereof.

Note that the compounds of the present invention are all of the "E" (entgegen) or "trans" form, that is, the (optionally substituted) 4-methoxy-phenyl group (styryl phenyl group) and the 3,5-dimethoxybenzoyl group (acyl phenyl group) are positioned "trans" with respect to one another on the carbon-carbon double bond of the prop-1-ene backbone.

Substituent R$^{ALK}$

R$^{ALK}$ is primary or secondary aliphatic saturated C$_{2-6}$alkyl.

The primary aliphatic saturated C$_2$alkyl is -Et:

The primary and secondary aliphatic saturated C$_3$alkyls are -nPr and -iPr:

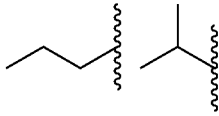

The primary and secondary aliphatic saturated C$_4$alkyls are -nBu, -iBu, -sBu:

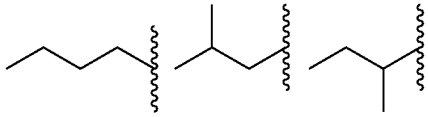

Examples of primary and secondary aliphatic saturated C$_5$alkyls include, but are not limited to:

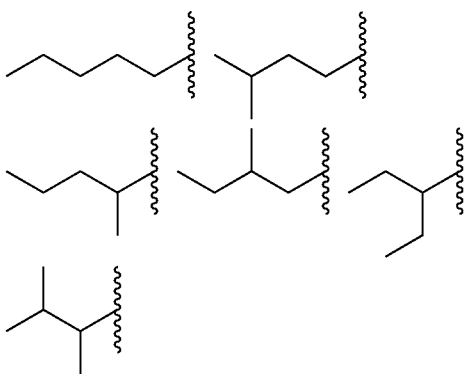

Examples of primary and secondary aliphatic saturated C$_5$alkyls include, but are not limited to:

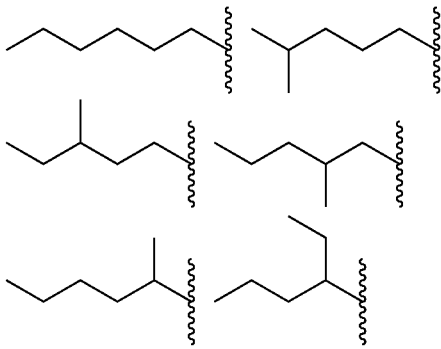

-continued

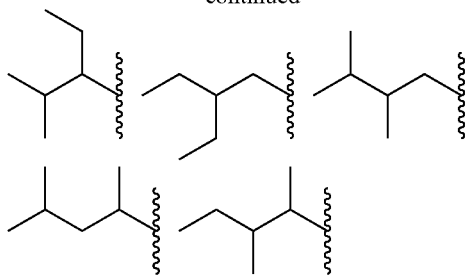

In one embodiment, $R^{ALK}$ is selected from: -Et, -nPr, -iPr, -nBu, -iBu, -sBu, -nPe, and -nHex.

In one embodiment, $R^{ALK}$ is selected from: -Et, -nPr, -nBu, -nPe, and -nHex.

Note that a reference to a particular primary or secondary aliphatic saturated $C_{2-6}$alkyl includes optical isomers thereof. For example, a reference to -sBu include both -sBu (R) and -sBu (S).

Substituents $R^{B2}$, $R^{B3}$, $R^{B4}$, and $R^{B5}$

Each of $R^{B2}$, $R^{B3}$, $R^{B4}$, and $R^{B5}$ is independently —H, —OH, or —OMe.

In one embodiment, one of $R^{B2}$, $R^{B3}$, $R^{B4}$, and $R^{B5}$ is —OH or —OMe, and the others are —H ("monosubstituted").

In one embodiment, two of $R^{B2}$, $R^{B3}$, $R^{B4}$, and $R^{B5}$ is —OH or —OMe, and the others are —H ("disubstituted").

In one embodiment, three of $R^{B2}$, $R^{B3}$, $R^{B4}$, and $R^{B5}$ is —OH or —OMe, and the other is —H ("trisubstituted").

In one embodiment, each of $R^{B2}$, $R^{B3}$, $R^{B4}$, and $R^{B5}$ is —OH or —OMe ("tetrasubstituted").

In one embodiment, one of $R^{B2}$, $R^{B3}$, $R^{B4}$, and $R^{B5}$ is —OMe, and the others are independently —H or —OH ("monomethoxy").

In one embodiment, two of $R^{B2}$, $R^{B3}$, $R^{B4}$, and $R^{B5}$ is —OMe, and the others are independently —H or —OH ("dimethoxy").

In one embodiment, two of $R^{B2}$, $R^{B3}$, $R^{B4}$, and $R^{B5}$ is —OMe, and the others are independently —H or —OH ("dimethoxy"); and the two —OMe groups are not adjacent to each other.

In one embodiment, two of $R^{B2}$, $R^{B3}$, $R^{B4}$, and $R^{B5}$ is —OMe; one of the others is —OH; and the last is —H ("dimethoxy-hydroxy").

In one embodiment, two of $R^{B2}$, $R^{B3}$, $R^{B4}$, and $R^{B5}$ is —OMe; one of the others is —OH; and the last is —H ("dimethoxy-hydroxy"); and the two —OMe groups are not adjacent to each other.

In one embodiment, three of $R^{B2}$, $R^{B3}$, $R^{B4}$, and $R^{B5}$ is —OMe, and the others are independently —H or —OH ("trimethoxy").

In one embodiment, each of $R^{B2}$, $R^{B3}$, $R^{B4}$, and $R^{B5}$ is —OMe ("tetramethoxy").

In one embodiment, each of $R^{B2}$, $R^{B3}$, $R^{B4}$, and $R^{B5}$ is independently —H or —OMe.

In one embodiment, one of $R^{B2}$, $R^{B3}$, $R^{B4}$, and $R^{B5}$ is —OMe, and the others are —H ("monosubstituted, monomethoxy").

In one embodiment, two of $R^{B2}$, $R^{B3}$, $R^{B4}$, and $R^{B5}$ is —OMe, and the others are —H ("disubstituted, dimethoxy").

In one embodiment, two of $R^{B2}$, $R^{B3}$, $R^{B4}$, and $R^{B5}$ is —OMe, and the others are —H ("disubstituted, dimethoxy"); and the two —OMe groups are not adjacent to each other.

In one embodiment, three of $R^{B2}$, $R^{B3}$, $R^{B4}$, and $R^{B5}$ is —OMe, and the other is —H ("trisubstituted, trimethoxy").

In one embodiment, the compound has one of the following formulae:

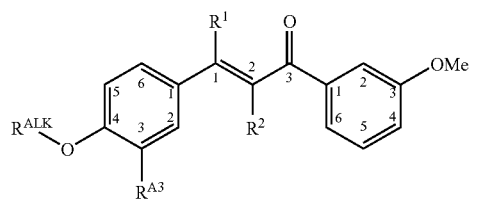
(2)

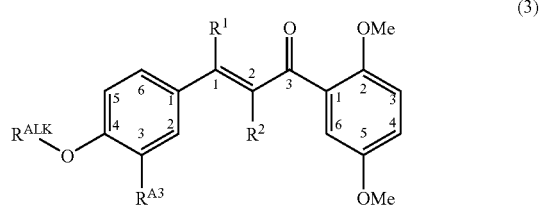
(3)

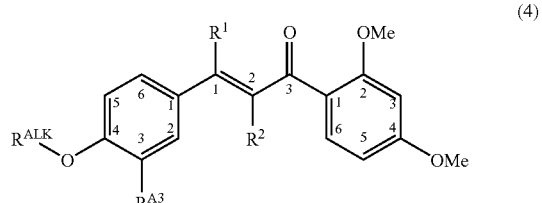
(4)

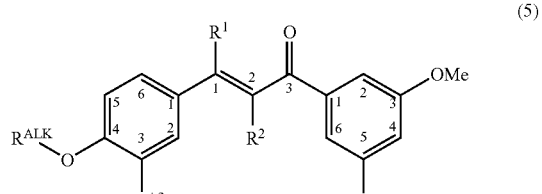
(5)

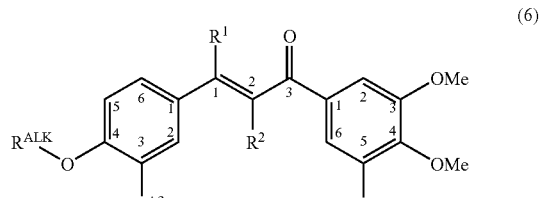
(6)

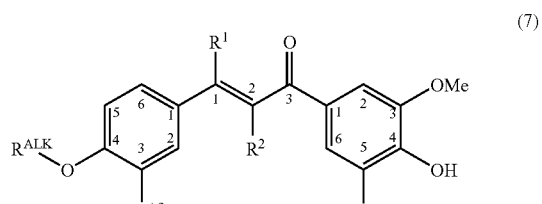
(7)

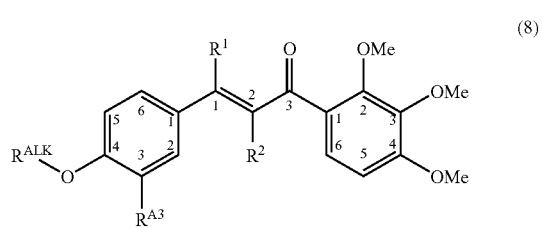
(8)

(9) 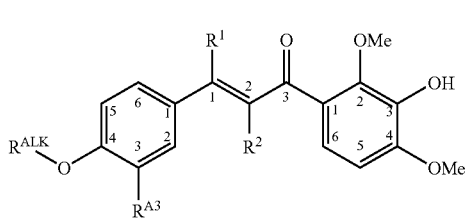

Substituents R¹ and R²

Each of R¹ and R² is independently —H, optionally substituted $C_{1-4}$alkyl, or optionally substituted $C_{5-20}$aryl.

In one embodiment, one of R¹ and R² is —H; and the other is —H, optionally substituted $C_{1-4}$alkyl, or optionally substituted $C_{5-20}$aryl.

In one embodiment, R¹ is —H; and R² is —H, optionally substituted $C_{1-4}$alkyl, or optionally substituted $C_{5-20}$aryl.

In one embodiment, R² is —H; and R¹ is —H, optionally substituted $C_{1-4}$alkyl, or optionally substituted $C_{5-20}$aryl.

In one embodiment, each of R¹ and R² is independently —H, -Me, or -Ph.

In one embodiment, one of R¹ and R² is —H; and the other is —H, -Me, or -Ph.

In one embodiment, R¹ is —H; and R² is —H, -Me, or -Ph.

In one embodiment, R² is —H; and R¹ is —H, -Me, or -Ph.

In one embodiment, each of R¹ and R² is independently —H or -Me.

In one embodiment, one of R¹ and R² is —H; and the other is —H or -Me.

In one embodiment, R¹ is —H; and R² is —H or -Me.

In one embodiment, R² is —H; and R¹ is —H or -Me.

In one embodiment, R¹ and R² are both —H:

(10) 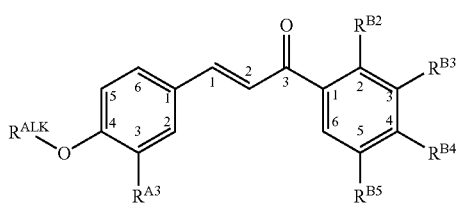

In one embodiment, R¹ and R² are both —H and the compound has one of the following formulae:

(11) 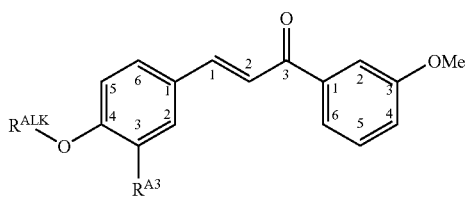

(12) 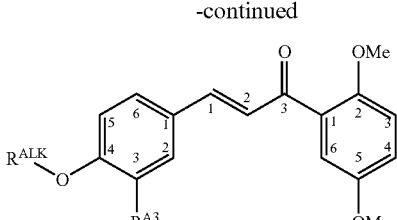

(13) 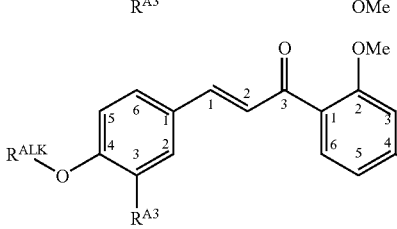

(14) 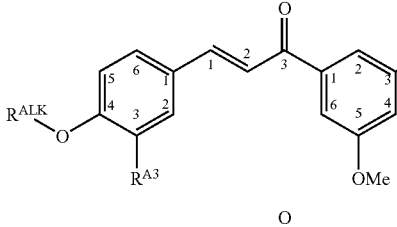

(15) 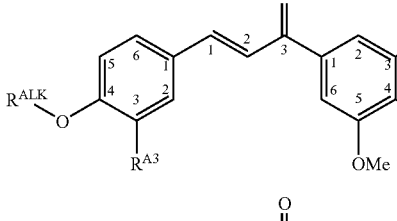

(16) 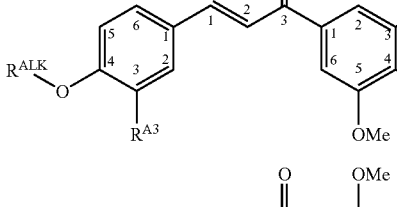

(17) 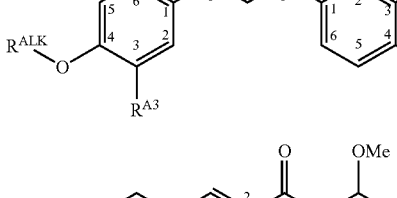

(18) 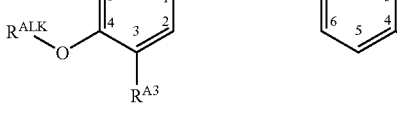

Substituent $R^{A3}$ $R^{A3}$ is —H, —OH, —OC(=O)$R^E$, —OS(=O)$_2$OH, or —OP(=O)(OH)$_2$, wherein $R^E$ is —H, optionally substituted $C_{1-6}$alkyl, optionally substituted $C_{3-20}$heterocyclyl, or optionally substituted $C_{5-20}$aryl.

In one embodiment, $R^E$ is selected from:

—CH$_3$ (so that —C(=O)$R^E$ is —C(=O)CH$_3$, acetyl);

—CH$_2$CH$_3$ (so that —C(=O)R$^E$ is —C(=O)CH$_2$CH$_3$, propionyl);
—C(CH$_3$)$_3$ (so that —C(=O)R$^E$ is —C(=O)C(CH$_3$)$_3$, pivaloyl); and
-Ph (so that —C(=O)R$^E$ is —C(=O)Ph, benzoyl).

In one embodiment, R$^{A3}$ is —OC(=O)R$^E$, —OS(=O)$_2$OH, or —OP(=O)(OH)$_2$. Such compounds may conveniently be referred to herein as "esterified compounds."

In one embodiment, R$^{A3}$ is —H, —OH, or —OC(=O)R$^E$.
In one embodiment, R$^{A3}$ is —H or —OH.
In one embodiment, R$^{A3}$ is —H, as shown below. Such compounds may conveniently be referred to herein as "non-hydroxylated compounds."

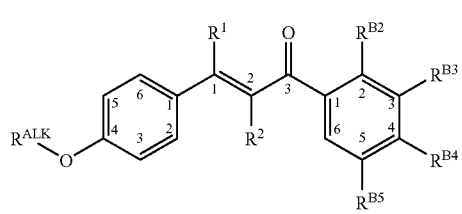
(19)

In one embodiment, R$^{A3}$ is —H and the compound has one of the following formulae:

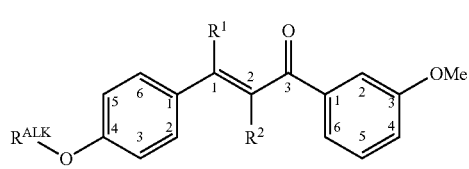
(20)

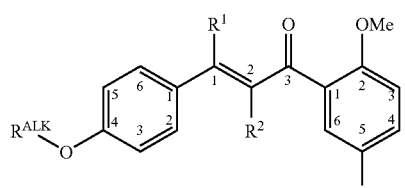
(21)

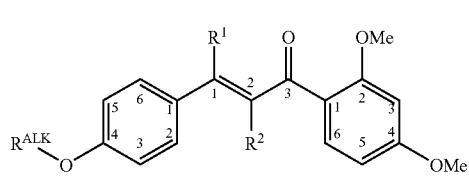
(22)

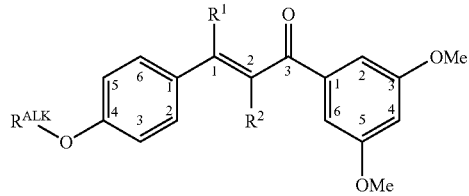
(23)

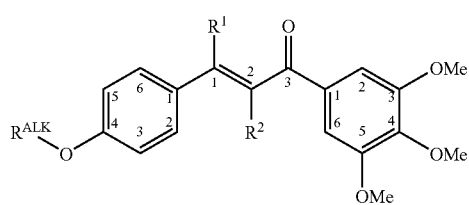
(24)

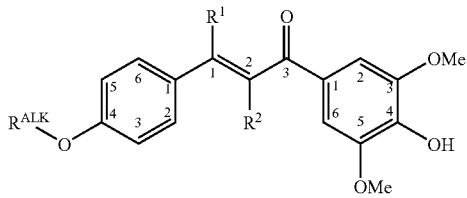
(25)

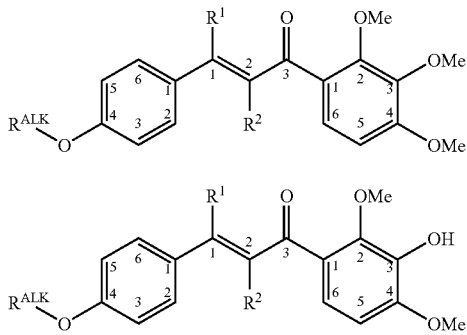
(26)

(27)

In one embodiment, R$^{A3}$ is —H; R$^1$ and R$^2$ are both —H; and the compound has one of the following formulae:

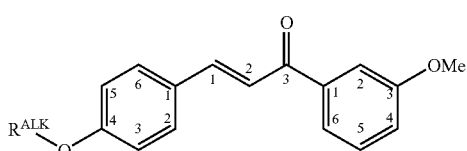
(28)

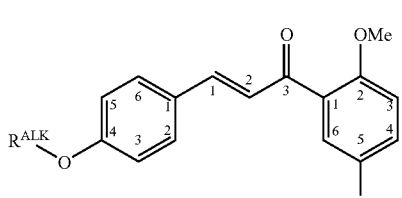
(29)

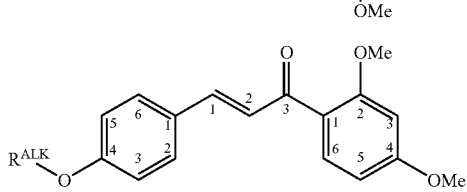
(30)

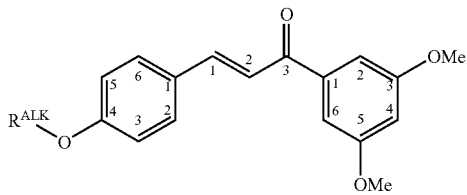
(31)

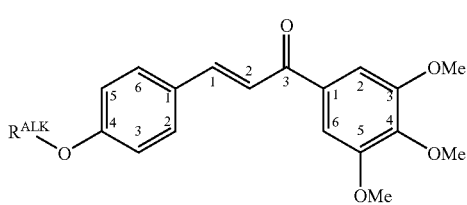
(32)

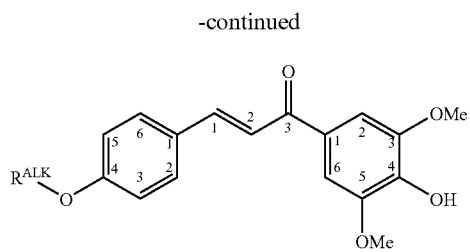
(33)
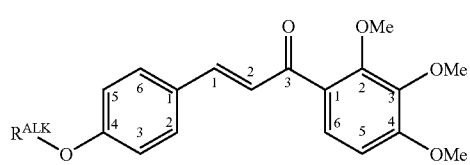
(34)
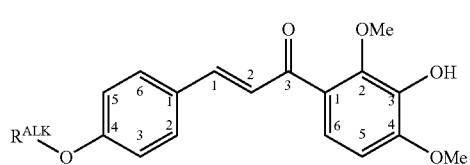
(35)
In one embodiment, $R^{A3}$ is —OH, as shown below. Such compounds may conveniently be referred to herein as "hydroxylated compounds."
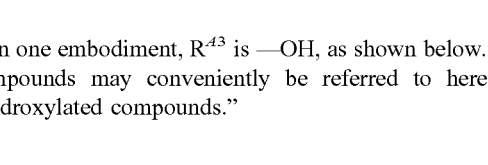
(36)
In one embodiment, $R^{A3}$ is —OH and the compound has one of the following formulae:
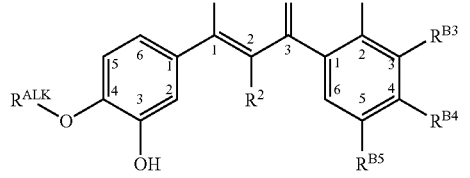
(37)
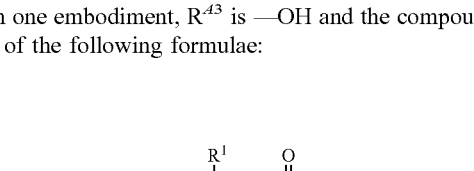
(38)
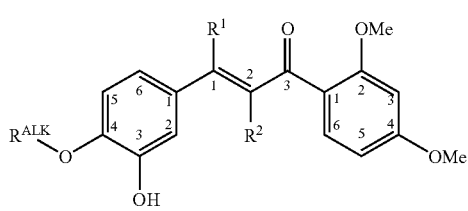
(39)
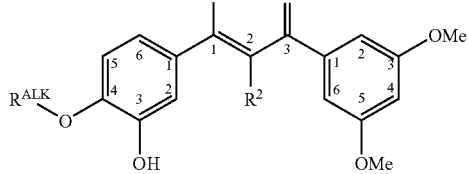
(40)
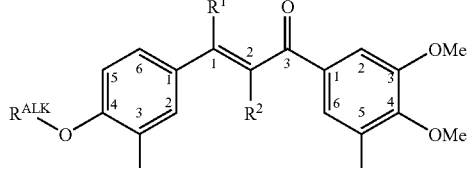
(41)
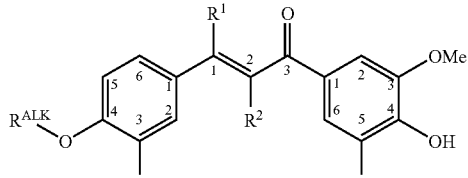
(42)
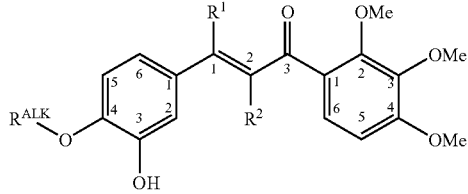
(43)
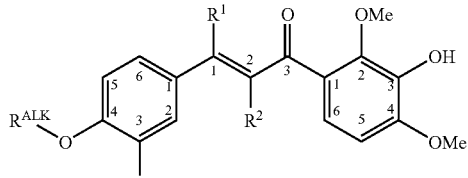
(44)
In one embodiment, $R^{A3}$ is —OH; $R^1$ and $R^2$ are both —H; and the compound has one of the following formulae:
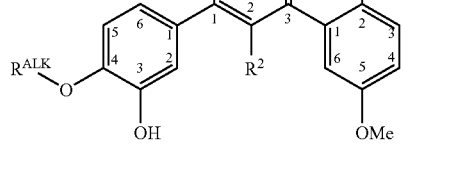
(45)

-continued
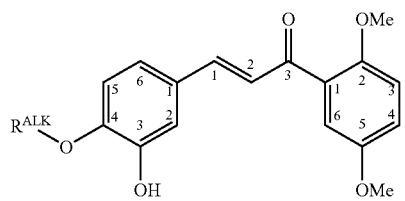
(46)
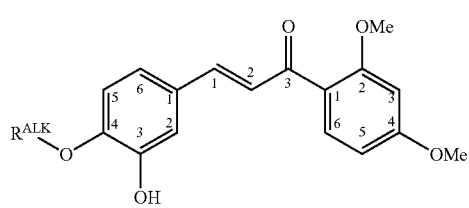
(47)
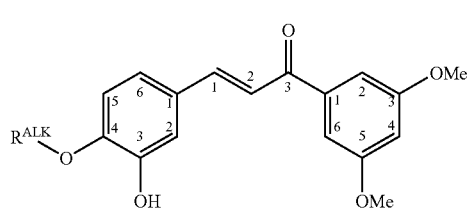
(48)
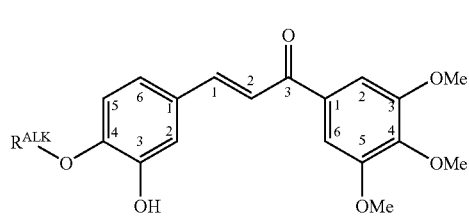
(49)
-continued
(50)
(51)
(52)
Some Specific Embodiments
Some specific embodiments of the present invention are shown below.
| 1 | 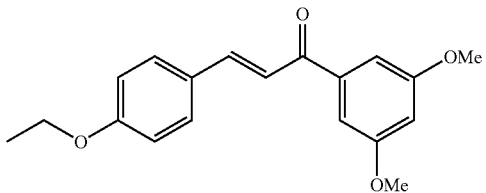 | DMU-174 |
| --- | --- | --- |
| 2 | 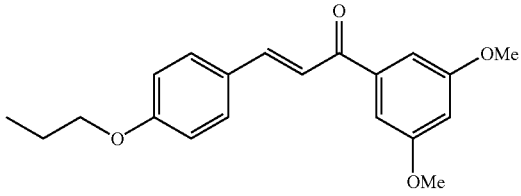 | DMU-175 |
| 3 | 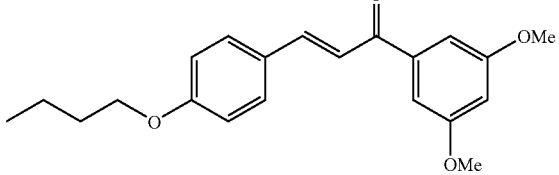 | DMU-176 |

-continued
| | | |
|---|---|---|
| 4 | 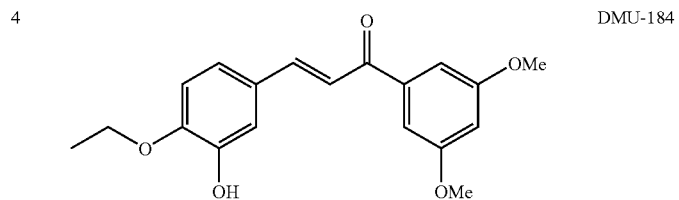 | DMU-184 |
| 5 | 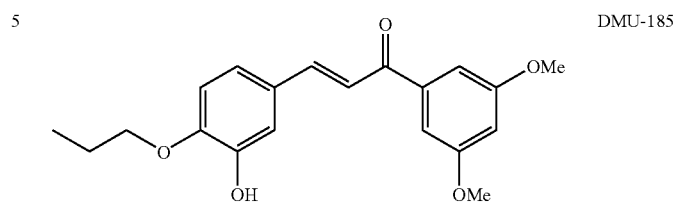 | DMU-185 |
| 6 | 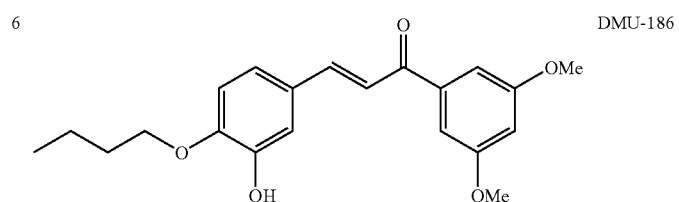 | DMU-186 |
| 7 | 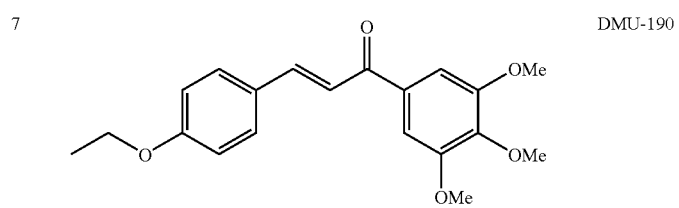 | DMU-190 |
| 8 | 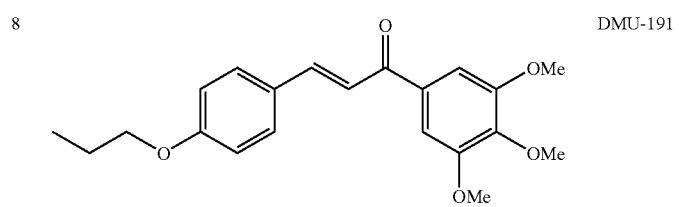 | DMU-191 |
| 9 | 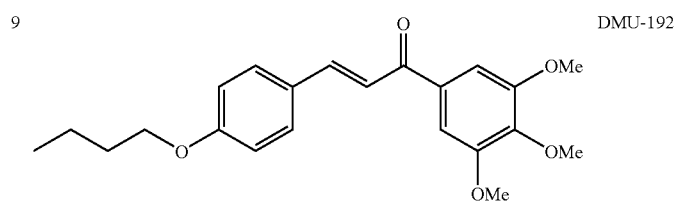 | DMU-192 |
| 10 | 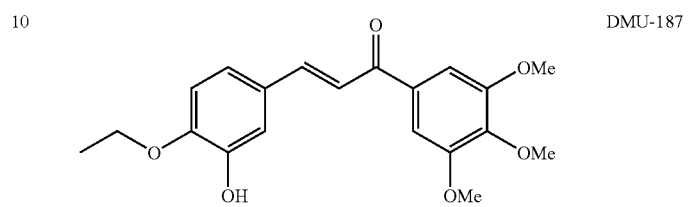 | DMU-187 |

-continued
| | | |
|---|---|---|
| 11 | 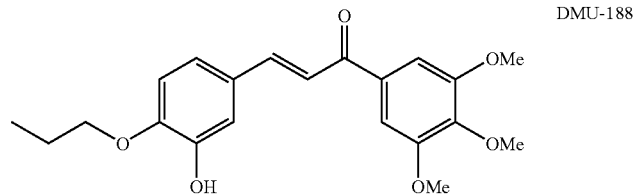 | DMU-188 |
| 12 | 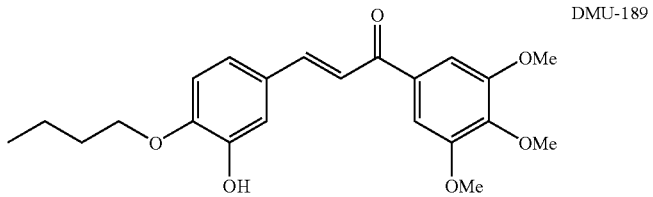 | DMU-189 |
| 13 | 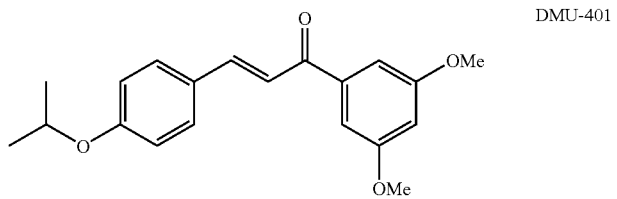 | DMU-401 |
| 14 | 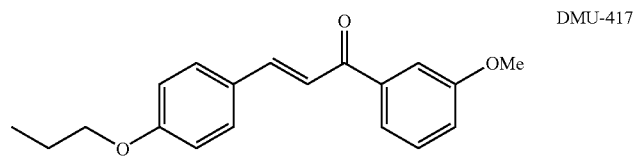 | DMU-417 |
| 15 | 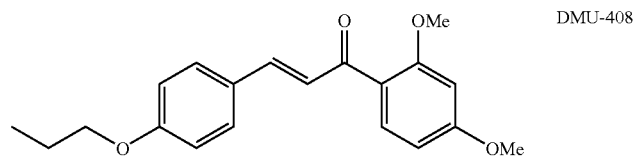 | DMU-408 |
| 16 | 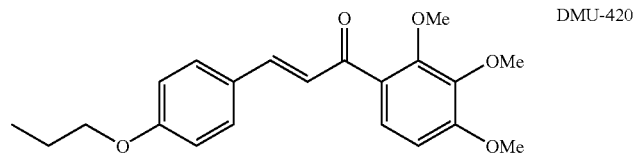 | DMU-420 |
| 17 | 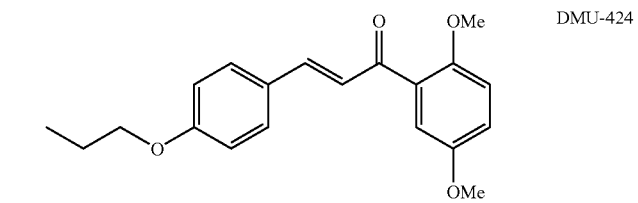 | DMU-424 |
| 18 | 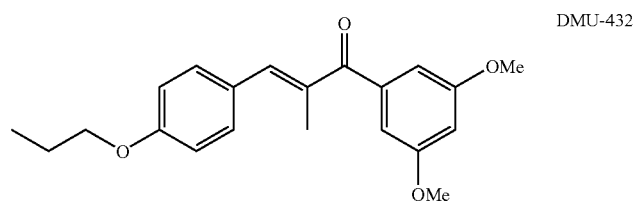 | DMU-432 |

Chemical Terms

The term "carbo," "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein at least one of said ring(s) is aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one preferred embodiment, the substituent(s) are independently selected from: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s) are independently selected from:

—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$, CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NMe$_2$; and, optionally substituted phenyl.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (also carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, cyclohexyl, and norbornane, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated C$_{1-7}$alkyl groups which have one or more carbon-carbon triple bonds (also referred to as "C$_{2-7}$alkynyl" groups) include, but are not limited to, ethynyl (ethinyl) and 2-propynyl (propargyl).

Examples of unsaturated alicyclic (also carbocyclic) C$_{1-7}$alkyl groups which have one or more carbon-carbon double bonds (also referred to as "C$_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Additional examples of substituted C$_{3-7}$cycloalkyl groups include, but are not limited to, those with one or more other rings fused thereto, for example, those derived from: indene (C$_9$), indan (2,3-dihydro-1H-indene) (C$_9$), tetraline (1,2,3,4-tetrahydronaphthalene (C$_{10}$), adamantane (C$_{10}$), decalin (decahydronaphthalene) (C$_{12}$), fluorene (C$_{13}$), phenalene (C$_{13}$). For example, 2H-inden-2-yl is a C$_5$cycloalkyl group with a substituent (phenyl) fused thereto.

C$_{3-20}$heterocyclyl: The term "C$_{3-20}$heterocyclyl," as used herein, pertains to a monovalent moiety obtained by removing a hydrogen atom from a ring atom of a C$_{3-20}$heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms.

In this context, the prefixes (e.g., C$_{3-20}$, C$_{3-7}$, C$_{5-6}$, etc.) denote the number of ring atoms, or range of number of ring atoms, whether carbon atoms or heteroatoms. For example, the term "C$_{5-6}$heterocyclyl," as used herein, pertains to a heterocyclyl group having 5 or 6 ring atoms. Examples of groups of heterocyclyl groups include C$_{3-20}$heterocyclyl, C$_{3-7}$heterocyclyl, C$_{5-7}$heterocyclyl.

Examples of (non-aromatic) monocyclic heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);

S$_1$: thiirane (C$_3$), thietane (C$_4$), thiolane (tetrahydrothiophene) (C$_5$), thiane (tetrahydrothiopyran) (C$_6$), thiepane (C$_7$);

O$_2$: dioxolane (C$_5$), dioxane (C$_6$), and dioxepane (C$_7$);

O$_3$: trioxane (C$_6$);

N$_2$: imidazolidine (C$_5$), pyrazolidine (diazolidine) (C$_5$), imidazoline (C$_5$), pyrazoline (dihydropyrazole) (C$_5$), piperazine (C$_6$);

N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);

N$_1$S$_1$: thiazoline (C$_5$), thiazolidine (C$_5$), thiomorpholine (C$_6$);

N$_2$O$_1$: oxadiazine (C$_6$);

O$_1$S$_1$: oxathiole (C$_5$) and oxathiane (thioxane) (C$_6$); and,

N$_1$O$_1$S$_1$: oxathiazine (C$_6$).

Examples of substituted (non-aromatic) monocyclic heterocyclyl groups include saccharides, in cyclic form, for example, furanoses (C$_5$), such as arabinofuranose, lyxofuranose, ribofuranose, and xylofuranose, and pyranoses (C$_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

C$_{5-20}$aryl: The term "C$_{5-20}$aryl," as used herein, pertains to a monovalent moiety obtained by removing a hydrogen atom from an aromatic ring atom of a C$_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms. In this context, the prefixes (e.g., C$_{3-20}$, C$_{5-7}$, C$_{5-6}$, etc.) denote the number of ring atoms, or range of number of ring atoms, whether carbon atoms or heteroatoms. For example, the term "C$_{5-6}$aryl," as used herein, pertains to an aryl group having 5 or 6 ring atoms. Examples of groups of aryl groups include C$_{3-20}$aryl, C$_{5-7}$aryl, C$_{5-6}$aryl.

The ring atoms may be all carbon atoms, as in "carboaryl groups" (e.g., C$_{5-20}$carboaryl).

Examples of carboaryl groups include, but are not limited to, those derived from benzene (i.e., phenyl) (C$_6$), naphthalene (C$_{10}$), azulene (C$_{10}$), anthracene (C$_{14}$), phenanthrene (C$_{14}$), naphthacene (C$_{18}$), and pyrene (C$_{16}$).

Examples of aryl groups which comprise fused rings, at least one of which is an aromatic ring, include, but are not limited to, groups derived from indene (C$_9$), isoindene (C$_9$), and fluorene (C$_{13}$).

Alternatively, the ring atoms may include one or more heteroatoms, including but not limited to oxygen, nitrogen, and sulfur, as in "heteroaryl groups." In this case, the group may conveniently be referred to as a "C$_{5-20}$heteroaryl" group, wherein "C$_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

N$_1$: pyrrole (azole) (C$_5$), pyridine (azine) (C$_6$);

O$_1$: furan (oxole) (C$_5$);

S$_1$: thiophene (thiole) (C$_5$);

N$_1$O$_1$: oxazole (C$_5$), isoxazole (C$_5$), isoxazine (C$_6$);

N$_2$O$_1$: oxadiazole (furazan) (C$_5$);

N$_3$O$_1$: oxatriazole (C$_5$);

N$_1$S$_1$: thiazole (C$_5$), isothiazole (C$_5$);

N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);

N$_3$: triazole (C$_5$), triazine (C$_6$); and,

N$_4$: tetrazole (C$_5$).

Examples of heterocyclic groups (some of which are also heteroaryl groups) which comprise fused rings, include, but are not limited to:

C$_9$heterocyclic groups (with 2 fused rings) derived from benzofuran (O$_1$), isobenzofuran (O$_1$), indole (N$_1$), isoindole (N$_1$), purine (N$_4$) (e.g., adenine, guanine), benzimidazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);

C$_{10}$heterocyclic groups (with 2 fused rings) derived from benzodioxan (O$_2$), quinoline (N$_1$), isoquinoline (N$_1$), benzoxazine ($N_1O_1$), benzodiazine ($N_2$), pyridopyridine ($N_2$), quinoxaline ($N_2$), quinazoline ($N_2$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)=(also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone (Cg) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$),
γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and –I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$hetercyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam, δ-valerolactam, and ε-caprolactam.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or –I, preferably —Cl, —Br, or –I.

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$alkyl group, a C$_{3-20}$heterocyclyl group, or a C$_{5-20}$aryl group, preferably a C$_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a C$_{1-7}$alkyl group, a C$_{3-20}$heterocyclyl group, or a C$_{5-20}$aryl group, preferably a C$_{1-7}$alkyl group, and R$^2$ is an acyl substituent, for example, a C$_{1-7}$alkyl group, a C$_{3-20}$heterocyclyl group, or a C$_{5-20}$aryl group, preferably a C$_{1-7}$alkyl group. Examples of acylamido groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

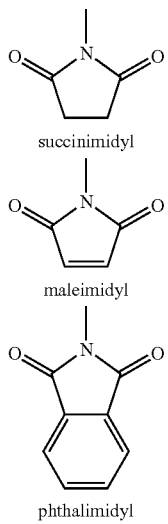

succinimidyl maleimidyl phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

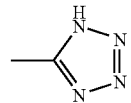

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh.

Examples of cyclic amino groups include, but are not limited to, aziridino, azetidino, piperidino, piperazino, morpholino, and thiomorpholino.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Sulfonic acid (sulfo): —S(=O)$_2$OH.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted groups are also discussed below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (as in toluene), xylyl (as in xylene), mesityl (as in mesitylene), styryl (as in styrene), and cumenyl (as in cumene).

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl), tolylmethyl, phenylethyl, and triphenylmethyl (trityl).

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

Some substituents are bidentate, that is, have two points for covalent attachment. For example, a bidentate group may be covalently bound to two different atoms on two different groups, thereby acting as a linker therebetween. Alternatively, a bidentate group may be covalently bound to two different atoms on the same group, thereby forming, together with the two atoms to which it is attached (and any intervening atoms, if present) a cyclic or ring structure. In this way, the bidentate substituent may give rise to a heterocyclic group/compound and/or an aromatic group/compound. Typically, the ring has from 3 to 8 ring atoms, which ring atoms are carbon or divalent heteroatoms (e.g., boron, silicon, nitrogen, phosphorus, oxygen, and sulfur, typically nitrogen, oxygen, and sulfur), and wherein the bonds between said ring atoms are single or double bonds, as permitted by the valencies of the ring atoms. Typically, the bidentate group is covalently bound to vicinal atoms, that is, adjacent atoms, in the parent group.

C$_{1-7}$alkylene: The term "C$_{1-7}$alkylene," as used herein, pertains to a bidentate moiety obtained by removing two hydrogen atoms, either both from the same carbon atom, or one from each of two different carbon atoms, of a C$_{1-7}$hydrocarbon compound having from 1 to 7 carbon atoms, which may be aliphatic or alicyclic, or a combination thereof, and which may be saturated, partially unsaturated, or fully unsaturated.

Examples of linear saturated C$_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$—(butylene).

Examples of branched saturated C$_{1-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{1-7}$alkylene groups include, but are not limited to, —CH=CH— (vinylene), —CH=CH—CH$_2$—, —CH=CH—CH$_2$—

CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, and —CH=CH—CH$_2$—CH$_2$—CH=CH—.

Examples of branched partially unsaturated C$_{1-7}$alkylene groups include, but are not limited to, —C(CH$_3$)=CH—, —C(CH$_3$)=CH—CH$_2$—, and —CH=CH—CH(CH$_3$)—.

Examples of alicyclic saturated C$_{1-7}$alkylene groups include, but are not limited to, cyclopentylene (e.g., cyclopent-1,3-ylene), and cyclohexylene (e.g., cyclohex-1,4-ylene).

Examples of alicyclic partially unsaturated C$_{1-7}$alkylene groups include, but are not limited to, cyclopentenylene (e.g., 4-cyclopenten-1,3-ylene), cyclohexenylene (e.g., 2-cyclohexen-1,4-ylene, 3-cyclohexen-1,2-ylene, 2,5-cyclohexadien-1,4-ylene).

C$_{5-20}$arylene: The term "C$_{5-20}$arylene," as used herein, pertains to a bidentate moiety obtained by removing two hydrogen atoms, one from each of two different ring atoms of a C$_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboarylene groups," in which case the group may conveniently be referred to as a "C$_{5-20}$carboarylene" group.

Alternatively, the ring atoms may include one or more heteroatoms, including but not limited to oxygen, nitrogen, and sulfur, as in "heteroarylene groups." In this case, the group may conveniently be referred to as a "C$_{5-20}$heteroarylene" group, wherein "C$_{5-20}$" denotes ring atoms, whether carbon atoms or heteroatoms. Preferably, each ring has from 5 to 7 ring atoms, of which from 0 to 4 are ring heteroatoms.

Examples of C$_{5-20}$arylene groups which do not have ring heteroatoms (i.e., C$_{5-20}$carboarylene groups) include, but are not limited to, those derived from benzene (i.e., phenyl) (C$_6$), naphthalene (C$_{10}$), anthracene (C$_{14}$), phenanthrene (C$_{14}$), and pyrene (C$_{16}$).

Examples of C$_{5-20}$heteroarylene groups include, but are not limited to, C$_5$heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and C$_6$heteroarylene groups derived from isoxazine, pyridine (azine), pyridazine (1,2-diazine), pyrimidine (1,3-diazine; e.g., cytosine, thymine, uracil), pyrazine (1,4-diazine), triazine, tetra-zole, and oxadiazole (furazan).

C$_{5-20}$Arylene-C$_{1-7}$alkylene: The term "C$_{5-20}$arylene-C$_{1-7}$alkylene," as used herein, pertains to a bidentate moiety comprising a C$_{5-20}$arylene moiety, -Arylene-, linked to a C$_{1-7}$alkylene moiety, -Alkylene-, that is, -Arylene-Alkylene-.

Examples of C$_{5-20}$arylene-C$_{1-7}$alkylene groups include, but are not limited to, phenylene-methylene, phenylene-ethylene, phenylene-propylene, and phenylene-ethenylene (also known as phenylene-vinylene).

C$_{5-20}$Alkylene-C$_{1-7}$arylene: The term "C$_{5-20}$alkylene-C$_{1-7}$arylene," as used herein, pertains to a bidentate moiety comprising a C$_{5-20}$alkylene moiety, -Alkylene-, linked to a C$_{1-7}$arylene moiety, -Arylene-, that is, -Alkylene-Arylene-.

Examples of C$_{5-20}$alkylene-C$_{1-7}$arylene groups include, but are not limited to, methylene-phenylene, ethylene-phenylene, propylene-phenylene, and ethenylene-phenylene (also known as vinylene-phenylene).

Included in the above are the well known ionic, salt, solvate (e.g., hydrate), and protected forms of these substituents. For example, a reference to carboxylic acid (—COOH) also includes carboxylate (—COO$^-$). Similarly, a reference to an amino group includes a salt, for example, a hydrochloride salt, of the amino group. A reference to a hydroxyl group also includes conventional protected forms of a hydroxyl group. Similarly, a reference to an amino group also includes conventional protected forms of an amino group.

Acronyms

For convenience, many chemical moieties are represented herein using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl(Ph), biphenyl (biPh), benzyl (Bn), naphthyl (naph), methoxy (MeO), ethoxy (EtO), benzoyl (Bz), and acetyl (Ac).

For convenience, many chemical compounds are represented herein using well known abbreviations, including but not limited to, methanol (MeOH), ethanol (EtOH), iso-propanol (i-PrOH), methyl ethyl ketone (MEK), acetic acid (AcOH), dichloromethane (methylene chloride, DCM), trifluoroacetic acid (TFA), dimethylformamide (DMF), and tetrahydrofuran (THF).

Isomers, Salts, Solvates, Protected Forms, and Prodrugs

A certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

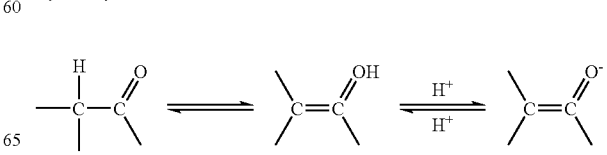

Note that specifically included in the term "isomer" are compounds with one or more isotopic substitutions. For example, H may be in any isotopic form, including $^1$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, ethylenediamine, ethanolamine, diethanolamine, piperazine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluenesulfonic, methanesulfonic, ethanesulfonic, ethane disulfonic, oxalic, isethionic, and valeric.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH$_3$, —OAc).

For example, an aldehyde or ketone group may be protected as an acetal or ketal, respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O*).

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; an acetamidomethyl ether (—S—CH$_2$NHC(═O)CH$_3$).

It may be convenient or desirable to prepare, purify, and/or handle the active compound in the form of a prodrug. The term "prodrug," as used herein, pertains to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis

Several methods for the chemical synthesis of compounds of the present invention are described herein. These methods may be modified and/or adapted in known ways in order to facilitate the synthesis of additional compounds within the scope of the present invention.

The compounds of the present invention may be prepared, for example, by Aldol condensation of the corresponding carbonyl compounds A and B, as illustrated below in Scheme 1.

Scheme 1

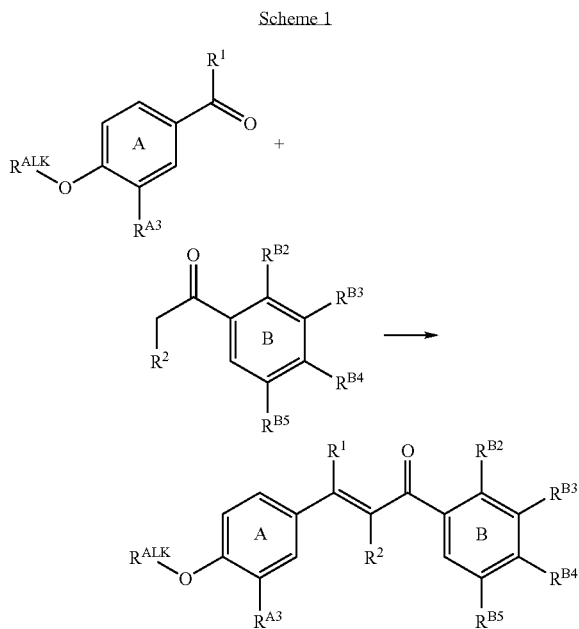

When $R^1$ is —H, the first compound is a 4-alkoxybenzaldehyde. When $R^2$ is —H, the second compound is an acetophenone.

Many suitable starting reagents are commercially available (e.g., from Sigma-Aldrich). Additional reagents may be synthesised using known methods, or by modifying known methods in known ways.

For example, compound DMU-174 may be prepared by stirring a mixture of 4-ethoxybenzaldehyde (A) and 3,5-dimethoxyacetophenone (B) in a suitable solvent, e.g., methanol, with added base catalyst, e.g., aqueous sodium hydroxide for 2 hours at ambient temperature. The reaction is illustrated below in Scheme 2.

Scheme 2

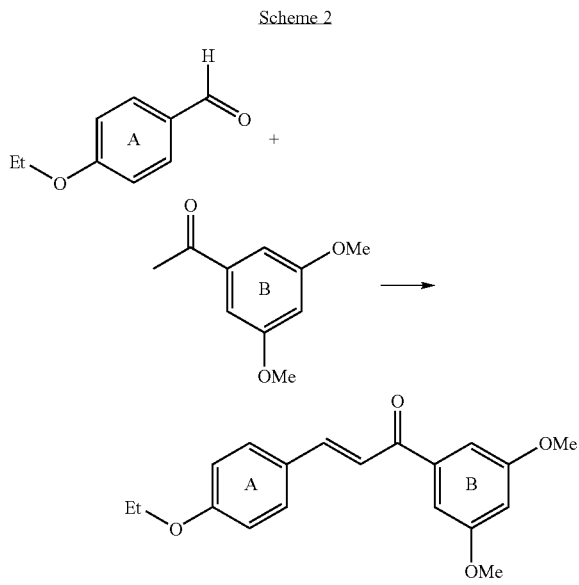

Compounds for which $R^{A3}$ is —OC(=O)$R^E$, —OS(=O)$_2$OH, or —OP(=O)(OH)$_2$ may be prepared from their hydroxy analogs (where $R^{A3}$ is —OH) by reaction with an organic acid (i.e., $R^E$COOH) or an inorganic acid (i.e., sulfuric acid, $H_2SO_4$; phosphoric acid, $H_3PO_4$).

The groups —OS(=O)$_2$OH and —OP(=O)(OH)$_2$ may be present as such, in their free acid form, or they may be present as a salt or ester thereof, as discussed above. For example, the group —OS(=O)$_2$OH may be present as —OS(=O)$_2$O$^-$ M$^+$, wherein M$^+$ is a suitable cation. Similarly, the group —OP(=O)(OH)$_2$ may be present as —OP(=O)(OH)O$^-$ M$^+$ or —OP(=O)(O$^-$)$_2$(M$^+$)$_2$, wherein M$^+$ is a suitable cation. Examples of suitable cations are discussed above. In one embodiment, the group —OP(=O)(OH)$_2$ is present as the disodium salt, —OP(=O)(O$^-$)$_2$(Na$^+$)$_2$. Other salts and esters are described in Pettit et al, 1995.

Uses

The present invention provides active compounds which are capable of regulating (e.g., inhibiting) cell proliferation, as well as methods of regulating (e.g., inhibiting) cell proliferation, comprising contacting a cell with an effective amount of an active compound, whether in vitro or in vivo.

The term "active," as used herein, pertains to compounds which are capable of regulating (e.g., inhibiting) cell proliferation, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active, that is, capable of regulating (e.g., inhibiting) cell proliferation. For example, assays which may conveniently be used to assess the proliferation regulation offered by a particular compound are described in the examples below.

For example, a sample of cells (e.g., from a tumour) may be grown in vitro and a candidate compound brought into contact with the cells, and the effect of the compound on those cells observed. As examples of "effect," the morphological status of the cells may be determined (e.g., alive or dead). Where the candidate compound is found to exert an influence on the cells, this may be used as a prognostic or diagnostic marker of the efficacy of the compound in methods of treating a patient carrying cells of the same type (e.g., the tumour or a tumour of the same cellular type).

In one aspect, the present invention provides antiproliferative agents. The term "antiproliferative agent" as used herein, pertains to a compound which treats a proliferative condition (i.e., a compound which is useful in the treatment of a proliferative condition).

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

In another embodiment, the proliferative condition is a solid tumour. In another embodiment, the proliferative condition is a solid tumour, and is a cancer of the lung, colon, breast, ovarian, prostate, liver, pancreas, brain, or skin. In another embodiment, the proliferative condition is a solid tumour, and is a cancer of the breast.

As discussed below (see "Prodrugs"), compounds of the present invention may act as prodrugs useful as antiproliferative agents with low intrinsic toxicity, for treatment of proliferative conditions which are characterised by cells which express the CYP1B1 enzyme.

Additionally, compounds of the present invention may act as prodrugs useful as selective antiproliferative agents with low intrinsic toxicity, for treatment of proliferative conditions which are characterised by cells which express the CYP1B1 enzyme, where the corresponding normal cells do not express the CYP1B1 enzyme.

Thus, in one preferred embodiment, the proliferative condition is characterised by cells which express CYP1B1. In one preferred embodiment, the proliferative condition is characterised by cells which express CYP1B1, where the corresponding normal cells do not express CYP1B1. For example, the proliferative condition may be a tumour characterised by tumour cells which express CYP1B1, where the corresponding normal cells do not.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The present invention also provides active compounds which are useful in the treatment of inflammatory conditions. For example, such compounds have growth down-regulatory effects on splenocytes. Examples of inflammaotry conditions include, but are not limited to, rheumatoid arthritis, rheumatic fever, osteoarthritis, inflammatory bowel disease, psoriasis, and bronchial asthma.

The invention further provides active compounds for use in a method of treatment of the human or animal body by therapy. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides the use of an active compound for the manufacture of a medicament, for example, for the treatment of a proliferative condition or an inflammatory condition, as discussed above.

The invention further provides a method for regulating (e.g., inhibiting) cell proliferation, comprising said cell with an effective amount of an active compound whether in vitro or in vivo.

Another aspect of the present invention pertains to methods of treating a proliferative condition in a subject comprising administering to said subject a therapeutically-effective amount of an active compound, preferably in the form of a pharmaceutical composition.

Active compounds may also be used, as described above, in combination therapies, that is, in conjunction with other agents, for example, cytotoxic agents.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, other antiinflammatory agents, etc.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active ingredient, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, lozenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, paste, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freese-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Prodrugs

Compounds of the present invention may be prodrugs for potent antiproliferative agents. Compounds which exhibit low or moderate intrinsic activity may act as prodrugs, and be metabolically activated (e.g., in vivo) to generate more potent compounds. This is especially useful in cancer therapy where metabolic activation can be achieved by an enzyme that is expressed in tumours.

For example, the cytochrome P450 enzyme CYP1B1 has been shown to be specifically expressed in tumour cells, but is not found in the corresponding normal tissues. This enzyme is found to be expressed in a variety of tumours, such as brain, breast, colon, stomach, ovarian and prostate cancers (see, e.g., Murray et al, 1997; Melvin et al., 1997). Prodrugs, acting as a substrate, may be metabolised by CYP1B1 through an aromatic hydroxylation reaction to generate a potent anticancer agent.

For example, as illustrated below, a prodrug, with low intrinsic activity (e.g., IC50 of 0.69 µM in breast cancer MCF-7 cells) (E)-1-(4-methoxyphenyl)-3-(3,5-dimethoxyphenyl)prop-1-en-3-one, is converted to the hydroxylated metabolite, (E)-1-(3-Hydroxy-4-methoxyphenyl)-3-(3,5-dimethoxyphenyl)prop-1-en-3-one, which has substantially potency (e.g., IC50 of 0.00065 µM in the same cell line).

Scheme 3

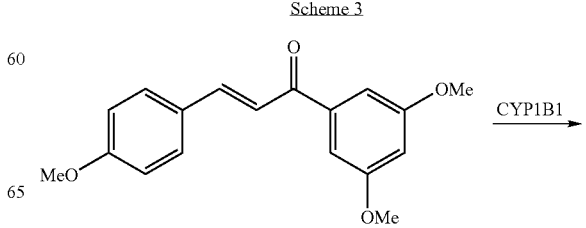

-continued

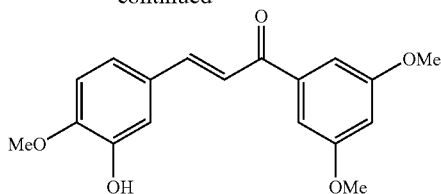

Thus, those compounds of the present invention where $R^{43}$ is —H may be prodrugs, to be activated by CYP1B1 enzyme, to yield the corresponding drug where $R^{43}$ is —OH.

In such cases, the prodrug is useful as an antiproliferative agent with low intrinsic toxicity, for treatment of proliferative conditions characterised by cells which express the CYP1B1 enzyme.

Additionally, the prodrug is useful as a selective antiproliferative agent with low intrinsic toxicity, for treatment of proliferative conditions characterised by cells which express the CYP1B1 enzyme, where the corresponding normal cells do not express the CYP1B1 enzyme.

Furthermore, prodrugs with low intrinsic cytotoxicity, which are only activated upon entering cells (e.g., tumour cells) containing the CYP1B1 enzyme, are not only useful for treating cancer, but also as a prophylactic, in cancer prevention (i.e., as a cancer preventative agent).

A method for detecting and/or demonstrating the conversion of a candidate prodrug to the corresponding drug is described next: A microsomal preparation of human tumour tissue expressing the CYP1B1 enzyme is prepared essentially as described by the method of Barrie et al., 1989. The experiment is carried out at 37° C., under yellow light. An array of 1.5 ml centrifuge tubes are set up in a water bath shaker under aerobic conditions. To each tube is then added 500 µl of pH 7.6 buffer (0.1 M $NaK_2PO_4$), followed by NADPH (5 µl of a 25 mM stock solution). The microsomal preparation (80 µl) is then added and the tubes pre-incubated for 5 min at 37° C. The prodrug is then added (10 µl of a 5 mM stock solution) and the preparation incubated for 1 h at 37° C. After 1 h the tubes are transferred to an ice/water cooling bath (0° C.). The tubes are then centrifuged at 15,000 rpm for 30 min. A sample of the supernatant (100 µl) is then taken and analysed by HPLC. HPLC conditions: Spherisorb C18 (25 cm×4.6 mm id), used without guard column. Flow rate 1 ml/min. Eluent 75% 0.1 M $KH_2PO_4$ and 25% acetonitrile. The hydroxylated drug is detected by HPLC, and confirmed by comparison with the authentic hydroxylated synthetic compound.

Diagnosis and Assays

In many cases, hydroxylated compounds, where $R^{43}$ is —OH, exhibit much greater fluorescence than the corresponding non-hydroxylated compound, where $R^{43}$ is —H. This property may be exploited in diagnosis, for example, of cancer, by detecting and/or measuring the formation of the hydroxylated metabolite via tumour cells expressing the CYP1B1 enzyme.

Thus, one aspect of the present invention pertains to a method of diagnosis of a subject for the presence of cells (e.g., tumour cells) expressing the CYP1B1 enzyme, comprising:

(a) administering to the patient a non-hydroxylated prodrug as described herein, wherein $R^{43}$ is —H;
(b) determining the amount of the corresponding hydroxylated metabolite, wherein $R^{43}$ is —OH which is subsequently produced; and,
(c) correlating the amount with the presence or absence of the cells in the patient.

Another aspect of the present invention pertains to active compounds, wherein $R^{43}$ is —H, for use in a method of diagnosis of the human or animal body. In one embodiment, the diagnosis is for the presence of cells (e.g., tumour cells) expressing the CYP1B1 enzyme.

Another aspect of the present invention pertains to use of active compounds, wherein $R^{43}$ is —H, for the manufacture of a composition, for example, for the diagnosis of the presence of cells (e.g., tumour cells) expressing the CYP1B1 enzyme, a proliferative condition, an inflammatory condition, etc., as discussed above.

Kits

One aspect of the invention pertains to a kit comprising (a) the active ingredient, preferably provided in a suitable container and/or with suitable packaging; and (b) instructions for use, for example, written instructions on how to administer the active compound, how to perform a diagnosis using the active compound, etc.

The written instructions may also include a list of indications for which the active ingredient is a suitable treatment.

EXAMPLES

The following are examples are provided solely to illustrate the present invention and are not intended to limit the scope of the invention, as described herein.

Analytical Methods

The $^1$H- and $^{13}$C-NMR spectra were recorded on a 250 MHz super-conducting Bruker AC250 Spectrometer. Infrared spectra were recorded in potassium bromide on a Shimadzu FTIR-8300 Spectrophotometer. The mass spectra were recorded on a VG 70 SEQ Spectrometer. Melting points were determined on an Electrothermal melting point apparatus and were uncorrected. Thin layer chromatography was performed on silica gel sheets (Merck TLC Aluminium sheet-Silica Gel 60F) and was monitored with UV light. Column chromatography was performed using Silica gel 60 (220–440 mesh).

Example 1

(E)-1-(4-ethoxyphenyl)-3-(3,5-dimethoxyphenyl) prop-1-en-3-one (DMU-174)

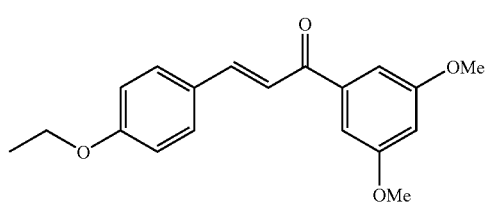

To a stirred solution of 4-ethoxybenzaldehyde (1.0 g, 6.6 mmol) and 3,5-dimethoxyacetophenone (1.19 g, 6.6 mmol) in methanol (10 ml) was added 50% w/v of aqueous sodium hydroxide (5.3 ml, 0.06 mol). The reaction mixture was stirred for 2 h at room temperature and then extracted with ethyl acetate (3×20 ml). The combined organic layers were dried over magnesium sulphate and reduced in vacuo and the product was recrystallised from ethanol to give 1.12 g (74%) of yellow crystals. $^1$H-NMR (CDCl$_3$) δ 7.8 (d, 1H), 7.6 (d, 2H), 7.3 (d, 1H), 7.15 (d, 2H), 6.9 (d, 2H), 6.65 (t, 1H), 4.0 (q, 2H), 3.8 (s, 6H), 1.4 (t, 3H). $^{13}$C-NMR (CDCl$_3$) δ 190.1, 161.1, 160.8, 140.6, 127.4, 63.6. Mass Spectrum m/e (M+1) 313.

Example 2

(E)-1-(4-propoxyphenyl)-3-(3,5-dimethoxyphenyl)prop-1-en-3-one (DMU-175)

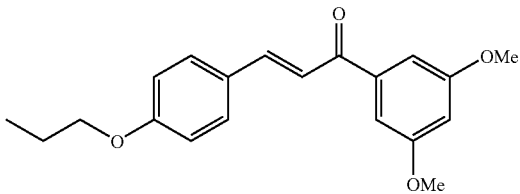

To a stirred solution of 4-propoxybenzaldehyde (0.5 g, 3.1 mmol) and 3,5-dimethoxyacetophenone (0.55 g, 3.1 mmol) in methanol (10 ml) was added 50% w/v of aqueous sodium hydroxide (2.4 ml, 0.031 mol). The reaction mixture was stirred for 2 h at room temperature and then extracted with ethyl acetate (3×20 ml), the combined organic layers were dried over magnesium sulphate and reduced in vacuo. The product was recrystallised from ethanol to give 0.978 g (93%) of off-white crystals. $^1$H-NMR (CDC$_3$) δ 7.8 (d, 1H), 7.6(d, 2H), 7.3 (d, 1H), 7.15 (d, 2H), 6.9 (d, 2H), 6.65 (t, 1H), 4.0 (t, 2H), 3.9 (s, 6H), 1.85 (m, 2H), 1.05 (t, 3H). $^{13}$C-NMR (CDCl$_3$) δ 190.2, 161.3, 160.8, 144.9, 140.6, 130.2, 127.4, 119.6, 114.9, 106.3, 104.8, 69.7, 55.6, 22.5, 10.4. Mass Spectrum m/e (M+1)327.

Example 3

(E)-1-(4-butoxyphenyl)-3-(3,5-dimethoxyphenyl)prop-1-en-3-one (DMU-176)

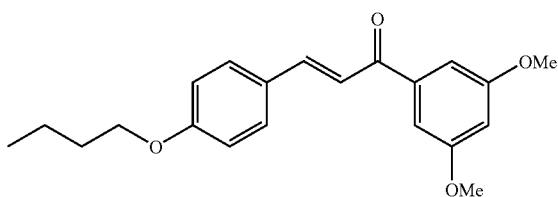

To a stirred solution of 4-butoxybenzaldehyde (0.5 g, 2.8 mmol) and 3,5-dimethoxyacetophenone (0.5 g, 2.8 mmol) in methanol (10 ml) was added 50% w/v of aqueous sodium hydroxide (2.24 ml, 0.028 mol). The reaction mixture was stirred for 2 h at room temperature and then extracted with ethyl acetate (3×20 ml), the combined organic layers were dried over magnesium sulphate and reduced in vacuo. The product was recrystallised from ethanol to give 0.925 g (97%) of off-white crystals. $^1$H-NMR (CDCl$_3$) δ 7.8 (d, 1H), 7.6 (d, 2H), 7.35 (d, 1H), 7.1 (d, 2H), 6.9 (d, 2H), 6.7 (t, 1H), 4.0 (t, 2H), 3.85 (s, 6H), 1.75 (m, 2H), 1.5 (m, 2H), 1.0 (t, 3H). $^{13}$C-NMR (CDCl$_3$) δ 191.1, 161.4, 160.8, 144.9, 140.8, 130.2, 127.3, 119.6, 114.9, 106.3, 104.8, 67.9, 55.6, 31.2, 19.2, 13.8. Mass Spectrum m/e (M+1) 341.

Example 4

(E)-1-(3-hydroxy-4-ethoxyphenyl)-3-(3,5-dimethoxyphenyl)prop-1-en-3-one (DMU-184)

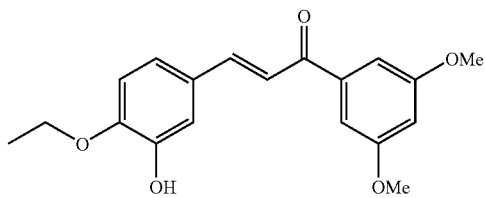

Anhydrous potassium carbonate (2.25 g, 16.3 mmol) was added to 3,4-dihydroxybenzaldehyde (1.5 g, 10.8 mmol), in butanone (30 ml), at room temperature. The reaction was stirred for 10 min after which ethyl iodide (0.872 ml, 10.8 mmol) was added dropwise and the reaction was refluxed for 3 h. The reaction mixture was diluted with water and the product was extracted with dichloromethane (3×25 ml), the combined organic layers were dried over magnesium sulphate and reduced in vacuo. Purification by column chromatography (SiO$_2$, petroleum:ether (40:60, v/v) with an increasing gradient of ethyl acetate) afforded 0.78 g (43%) of 3-hydroxy-4-ethoxybenzaldehyde as a white solid.

A mixture of 3-hydroxy-4-ethoxybenzaldehyde (0.413 g, 2.5 mmol), 3,5-dimethoxyacetophenone (0.448 mg, 2.5 mmol) and 50% w/v of aqueous sodium hydroxide (3.98 ml, 0.049 mol) in methanol (5 ml) at room temperature for 18 h. The yellow solid that precipitated was filtered and sequentially washed with cold methanol and ether and finally dried in a vacuum dessicator. Purification by column chromatography (SiO$_2$, petroleum:ether (40:60 v/v) with an increasing gradient of ethyl acetate) yielded 0.29 g (36%) of a yellow solid. $^1$H-NMR (CDCl$_3$) δ 7.7 (d, 1H), 7.2 (m, 2H), 7.1 (d, 3H), 6.8 (d, 1H), 6.5 (t, 1H), 5.7 (s, 1H), 4.1 (q, 2H), 3.9 (s, 6H), 1.4 (t, 3H). $^{13}$C-NMR (CDCl$_3$) δ 190.1, 160.9, 148.2, 146.1, 144.9, 140.6, 128.5, 122.7, 120.3, 113.1, 111.4, 106.3, 105.0, 64.7, 55.7, 14.8. Mass Spectrum m/e (M+1) 329. Anal. Calcd. for C$_{19}$H$_{20}$O$_5$.0.5H$_2$O: C, 69.5; H, 6.14. Found C, 69.62; H, 6.16.

Example 5

(E)-1-(3-hydroxy-4-propoxyphenyl)-3-(3,5-dimethoxyphenyl)prop-1-en-3-one (DMU-185)

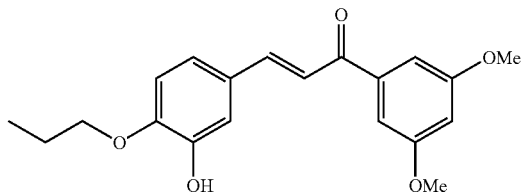

Anhydrous potassium carbonate (1.5 g, 10.8 mmol) and sodium iodide (0.108 g, 0.72 mmol) were added to 3,4-dihydroxybenzaldehyde (1.0 g, 7.2 mmol), in butanone (50 ml), at room temperature. The reaction was stirred for 10 min after which propyl bromide (0.657 ml, 7.2 mmol) was added dropwise and the reaction was refluxed for 3 h. The reaction mixture was diluted with water and the product was extracted with dichloromethane (3×25 ml), the combined organic layers were dried over magnesium sulphate and reduced in vacuo. Purification by column chromatography (SiO$_2$, petroleum:ether (40:60 v/v) with an increasing gradient of ethyl acetate) afforded 0.248 g (22%) of 3-hydroxy-4-propoxybenzaldehyde as an off-white solid.

A mixture of 3-hydroxy-4-propoxybenzaldehyde (0.4 g, 2.1 mmol), 3,5-dimethoxyacetophenone (0.371 mg, 2.1 mmol) and 50% w/v of aqueous sodium hydroxide (3.3 ml, 0.206 mol) in methanol (10 ml) at room temperature for 18 h. The yellow solid that precipitated was filtered and sequentially washed with cold methanol and ether and finally dried in a vacuum dessicator. Purification was achieved using column chromatography (SiO$_2$, petroleum:ether (40:60 v/v) with an increasing gradient of ethyl acetate) which gave 0.95 g (19%) of a yellow solid. $^1$H-NMR (CDCl$_3$) δ 7.7 (d, 1H), 7.3 (m, 2H), 7.1 (d, 3H), 6.8 (d, 1H), 6.6 (d, 1H), 5.7 (s, 1H), 4.1 (t, 2H), 3.9 (s, 6H), 1.9 (m, 2H), 1.0 (t, 3H). $^{13}$C-NMR (CDCl$_3$) δ 160.9, 146.0, 144.9, 128.4, 122.6, 120.2, 112.9, 106.2, 104.9, 70.6, 55.6, 22.4, 10.4. Mass Spectrum m/e (M+1) 343. Anal. Calcd. for C$_{20}$H$_{22}$O$_5$: C, 70.16; H, 6.48. Found C, 70.08; H, 6.38.

Example 6

(E)-1-(3-hydroxy-4-butoxyphenyl)-3-(3,5-dimethoxyphenyl)prop-1-en-3-one (DMU-186)

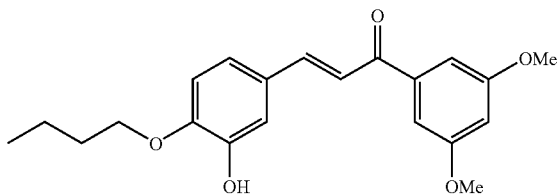

Anhydrous potassium carbonate (1.5 g, 5.4 mmol) and sodium iodide (0.108 g, 0.36 mmol) were added to 3,4-dihydroxybenzaldehyde (0.5 g, 3.6 mmol), In butanone (25 ml), at room temperature. The reaction was stirred for 10 min after which butyl bromide (0.777 ml, 3.6 mmol) was added dropwise and the reaction was refluxed for 3 h. The reaction mixture was diluted with water and the product was extracted with dichloromethane (3×25 ml), the combined organic layers were dried over magnesium sulphate and reduced in vacuo. Purification by column chromatography (SiO$_2$, petroleum:ether (40:60 v/v) with an increasing gradient of ethyl acetate) afforded 0.5 g (71%) of 3-hydroxy-4-butoxybenzaldehyde as an off-white solid.

A mixture of 3-hydroxy-4-butoxybenzaldehyde (0.4 g, 2.1 mmol), 3,5-dimethoxyacetophenone (0.371.9, 2.1 mmol) and 50% w/v of aqueous sodium hydroxide (3.3 ml, 0.206 mol) in methanol (10 ml) at room temperature for 18 h. The yellow solid that precipitated was filtered and sequentially washed with cold methanol and ether and finally dried in a vacuum dessicator. Purification was achieved using column chromatography (SiO$_2$, petroleum:ether (40:60 v/v) with an increasing gradient of ethyl acetate) which gave 0.36 g (50%) of a yellow solid: $^1$H-NMR (CDCl$_3$) δ 7.7 (d, 1H), 7.3 (m, 2H), 7.1 (d, 3H), 6.8 (d, 1H), 6.7 (d, 1H), 5.7 (s, 1H), 4.1 (t, 2H), 3.9 (s, 6H), 1.8 (m, 2H), 1.5 (m, 2H), 1.0 (t, 3H). $^{13}$C-NMR (CDCl$_3$) δ 190.0, 160.9, 148.3, 146.0, 144.9, 140.5, 128.4, 122.6, 120.2, 112.9, 111.4, 106.2, 104.9, 68.8, 55.6, 31.1, 19.1. 13.7. Mass Spectrum m/e (M+1) 357. Anal. Calcd. for C$_{21}$H$_{24}$O$_5$: C, 70.77, H, 6.79. Found C, 70.84; H, 6.81.

Example 7

(E)-1-(4-ethoxyphenyl)-3-(3,4,5-trimethoxyphenyl)prop-1-en-3-one (DMU-190)

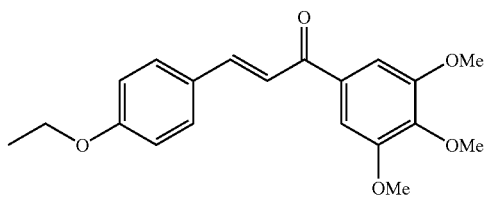

To a stirred solution of 4-ethoxybenzaldehyde (1.32 ml, 9.5 mmol) and 3,4,5-trimethoxyacetophenone (2.0 g, 9.5 mmol) in methanol (30 ml) was added 50% w/v of aqueous sodium hydroxide (7.6 ml, 0.095 mol). The reaction was stirred for 24 h at room temperature. A precipitate was isolated by filtration, washed with pet:ether and subsequently recrystallised from ethanol. 1.8 g (55%) of a pale yellow powder was isolated. $^1$H-NMR (CDCl$_3$) δ 7.8 (d, 1H), 7.6 (d, 2H), 7.3 (d, 1H), 6.9 (d, 2H), 4.1 (q, 2H), 3.9 (s×2, 9H), 1.4 (t, 3H). $^{13}$C-NMR (CDCl$_3$) δ 189.2, 161.1, 153.1, 142.3, 133.8, 127.4, 63.4. Mass Spectrum m/e (M+1) 343.

Example 8

(E)-1-(4-propoxyphenyl)-3-(3,4,5-trimethoxyphenyl)prop-1-en-3-one (DMU-191)

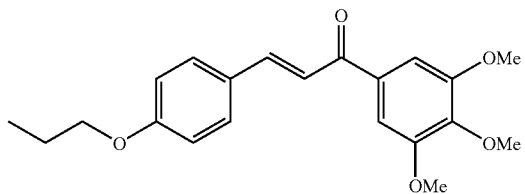

To a stirred solution of 4-propoxybenzaldehyde (1.5 ml, 9.5 mmol) and 3,4,5-trimethoxyacetophenone (2.0 g, 9.5 mmol) in methanol (30 ml) was added 50% w/v of aqueous sodium hydroxide (7.6 ml, 0.095 mol). The reaction was stirred for 24 h at room temperature. A precipitate was isolated by filtration, washed with pet:ether and subsequently recrystallised from ethanol to give 0.9 g (27%) of a pale yellow powder. $^1$H-NMR (CDCl$_3$) δ 7.8 (d, 1H), 7.6 (d, 2H), 7.3 (d, 1H), 7.2 (m, 1H), 6.8 (d, 2H), 3.95 (m, 2H), 3.9 (s×2, 9H), 1.8 (t, 2H), 1.0 (t, 3H).

$^{13}$C-NMR (CDCl$_3$) δ 189.3, 161.3, 156.9, 153.1, 144.7, 142.4, 133.8, 130.1, 127.4, 119.3, 114.9, 106.1, 69.7, 60.9, 56.3, 22.5, 10.4. Mass Spectrum m/e (M+1) 357.

Example 9

(E)-1-(4-butoxyphenyl)-3-(3,4,5-trimethoxyphenyl)prop-1-en-3-one (DMU-192)

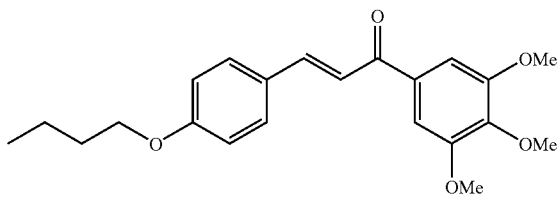

To a stirred solution of 4-butoxybenzaldehyde (1.64 ml, 9.5 mmol) and 3,4,5-trimethoxyacetophenone (2.0 g, 9.5 mmol) in methanol (30 ml) was added 50% w/v of aqueous sodium hydroxide (7.6 ml, 0.095 mol). The reaction was stirred for 24 h at room temperature. A precipitate was isolated by filtration, washed with pet:ether and subsequently recrystallised from ethanol to give 3.0 g (85%) of a pale yellow powder. $^1$H-NMR (CDCl$_3$) δ 7.8 (d, 1H), 7.6 (d, 2H), 7.4 (d, 1H), 7.25 (d, 2H), 7.0 (d, 2H), 4.05 (t, 2H), 4.0 (s×2, 9H), 1.8 (m, 2H), 1.5 (m, 2H), 1.0 (t, 3H). Mass Spectrum m/e (M+1) 370.

Example 10

(E)-1-(3-hydroxy4-ethoxyphenyl)-3-(3,4,5-trimethoxyphenyl)prop-1-en-3-one (DMU-187)

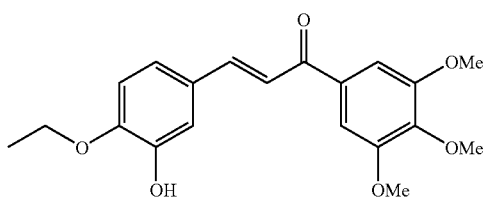

Anhydrous potassium carbonate (2.25 g, 16.3 mmol) was added to 3,4-dihydroxybenzaldehyde (1.5 g, 10.8 mmol), in butanone (30 ml), at room temperature. The reaction was stirred for 10 min after which ethyl iodide (0.872 ml, 10.8 mmol) was added dropwise and the reaction was refluxed for 3 h. The reaction mixture was diluted with water and the product was extracted with dichloromethane (3×25 ml), the combined organic layers were dried over magnesium sulphate and reduced in vacuo. Purification by column chromatography (SiO$_2$, petroleum:ether (40:60) with an increasing gradient of ethyl acetate) afforded 0.78 g (43%) of 3-hydroxy4-ethoxybenzaldehyde as a white solid.

A mixture of 3-hydroxy-4-ethoxybenzaldehyde (0.350 g, 2.5 mmol), 3,4,5-trimethoxyacetophenone (0.443 mg, 2.5 mmol) and 50% w/v of aqueous sodium hydroxide (3.37 ml, 0.042 mol) in methanol (5 ml) at room temperature for 18 h. An orange solid was isolated by filtration, dissolved in ethyl acetate which was subsequently dried over MgSO$_4$ and reduced in vacuo. Purification by column chromatography (SiO$_2$, petroleum:ether (40:60 v/v) with an increasing gradient of ethyl acetate) yielded 0.126 g (16.7%) of a yellow solid. $^1$H-NMR (CDCl$_3$) δ 7.7 (d, 1H), 7.3 (m, 4H), 7.1 (dd, 1H), 6.9 (d, 1H), 5.75 (s, 1H), 4.2 (q, 2H), 3.95 (s×2, 9H), 1.5 (t, 3H). $^{13}$C-NMR (CDCl$_3$) δ 190.0, 153.1, 150.0, 146.0, 133.7, 128.4. Mass Spectrum m/e (M+1) 359. Anal. Calcd. for C$_{20}$H$_{22}$O$_6$: C, 67.03; H, 6.19. Found C, 66.74; H, 6.33.

Example 11

(E)-1-(3-hydroxy4-propoxyphenyl)-3-(3,4,5-trimethoxyphenyl)prop-1-en-3-one (DMU-188)

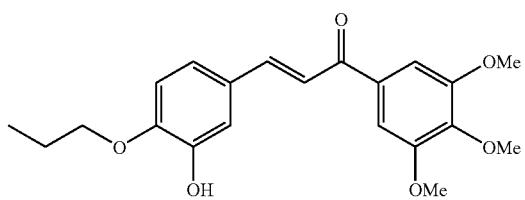

Anhydrous potassium carbonate (5.9 g, 0.043 mmol) and sodium iodide (0.434 g, 4.3 mmol) were added to 3,4-dihydroxybenzaldehyde (4.0 g, 28.9 mmol), in butanone (100 ml), at room temperature. The reaction was stirred for 10 min after which propyl bromide (2.628 ml, 28.9 mmol) was added dropwise and the reaction was refluxed for 3 h. The reaction mixture was diluted with water and the product was extracted with dichloromethane (3×50 ml), the combined organic layers were dried over magnesium sulphate and reduced in vacuo. Purification by column chromatography (SiO$_2$, petroleum:ether (40:60 v/v) with an increasing gradient of ethyl acetate) afforded 1.21 g (23.3%) of 3-hydroxy-4-propoxybenzaldehyde as an off-white solid.

A mixture of 3-hydroxy-4-propoxybenzaldehyde (0.8 g, 4.4 mmol), 3,4,5-trimethoxyacetophenone (0.934 mg, 4.4 mmol) and 50% w/v of aqueous sodium hydroxide (7.0 ml, 0.089 mol) in methanol (10 ml) at room temperature for 18 h. The orange solid isolated by filtration was washed sequentially with cold methanol and ether and finally dried in a vacuum dessicator. Purification was achieved using column chromatography (SiO$_2$, petroleum:ether (40:60 v/v) with an increasing gradient of ethyl acetate) which gave 0.995 g (60%) of a yellow solid. $^1$H-NMR (CDCl$_3$) δ 7.7 (d, 1H), 7.2 (m, 4H), 7.1 (dd, 3H), 6.9 (d, 1H), 5.7 (s, 1H), 4.1 (t, 2H), 3.9 (s×2, 9H), 1.9 (m, 2H), 1.1 (t, 3H). $^{13}$C-NMR (CDCl$_3$) δ 189.1, 153.1, 148.3, 146.0, 144.7, 142.4, 133.7, 128.4, 122.9, 119.8, 112.7, 111.4, 106.1, 70.6, 60.9, 56.4, 22.4, 10.4. Mass Spectrum m/e (M+1) 373. Anal. Calcd. for C$_{21}$H$_{24}$O$_6$: C, 67.73; H, 6.5. Found C, 68.01; H, 6.72.

Example 12

(E)-1-(3-hydroxy-4-butoxyphenyl)-3-(3,4,5-trimethoxyphenyl)prop-1-en-3-one (DMU-189)

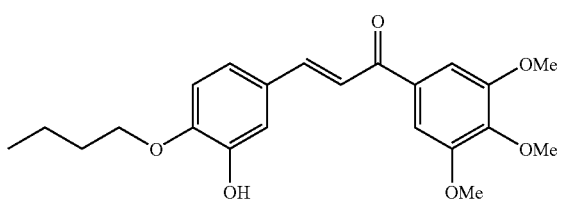

Anhydrous potassium carbonate (5.9 g, 0.0434 mmol) and sodium iodide (0.434 g, 2.9 mmol) were added to 3,4- dihydroxybenzaldehyde (4.0 g, 28.9 mmol), in butanone (100 ml), at room temperature. The reaction was stirred for 10 min after which butyl bromide (3.11 ml, 28.9 mmol) was added dropwise and the reaction was refluxed for 3 h. The reaction mixture was diluted with water and the product was extracted with dichloromethane (3×50 ml), the combined organic layers were dried over magnesium sulphate and reduced in vacuo. Purification by column chromatography (SiO$_2$, petroleum:ether (40:60 v/v) with an increasing gradient of ethyl acetate) afforded 2.25 g (58%) of 3-hydroxy-4-butoxybenzaldehyde as an off-white solid.

A mixture of 3-hydroxy-4-butoxybenzaldehyde (1.0 g, 5.2 mmol), 3,4,5-trimethoxyacetophenone (1.08 g, 5.2 mmol) and 50% w/v of aqueous sodium hydroxide (8.25 ml, 0.103 mol) in methanol (10 ml) at room temperature for 18 h. An orange solid was isolated by filtration and was sequentially washed with cold methanol and ether and finally dried in a vacuum dessicator. Purification was achieved using column chromatography (SiO$_2$, petroleum:ether (40:60 v/v) with an increasing gradient of ethyl acetate) which gave 0.224 g (11.3%) of a yellow solid: $^1$H-NMR (CDCl$_3$) δ 7.7 (d, 1H), 7.3 (m, 4H), 7.1 (dd, 1H), 6.9 (d, 1H), 5.7 (t, 1H), 5.7 (s, 1H), 4.1 (t, 2H), 4.0 (s×2, 9H), 1.8 (m, 2H), 1.5 (m, 2H), 1.0 (t, 3H). $^{13}$C-NMR (CDCl$_3$) δ 189.1, 157.6, 153.2, 146.1, 144.7, 133.8, 122.9, 119.9, 112.7, 111.4, 106.1, 68.9, 60.9, 56.4, 31.2, 19.2, 15.01, 13.8. Mass Spectrum m/e (M+1) 387. Anal. Calcd. for C$_{22}$H$_{26}$O$_6$: C, 68.38; H, 6.78. Found C, 68.57; H, 7.01.

Example 13

(E)-1-(4-isopropoxyphenyl)-3-(3,5-dimethoxyphenyl)prop-1-en-3-one (DMU-401)

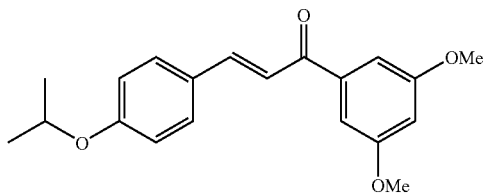

To a stirred solution of 4-isopropoxybenzaldehyde (1.0 g, 6.09 mmol) and 3,5-dimethoxyacetophenone (1.1 g, 6.09 mmol) in methanol (30 ml) was added a 50% w/v solution of aqueous sodium hydroxide (11 ml, 0.138 mol). The reaction mixture was stirred for 24 h at room temperature; no precipitate was observed. The product was extracted with ethyl acetate (3×50 ml), the combined organic layers were dried over anhydrous magnesium sulphate and reduced in vacuo. Purification by column chromatography (SiO$_2$, petroleum:ether (40:60 v/v) with an increasing gradient of ethyl acetate) afforded a yellow oil which was triturated with hexane to give a pale yellow solid (1.14 g, 57%). $^1$H-NMR (CDCl$_3$) δ 7.7 (d, 1H), 7.5 (m, 2H), 7.3 (d, 1H), 7.1 (d, 2H), 6.9 (m, 2H), 6.5 (t, 1H) 4.6 (m, 1H), 3.85 (s, 6H), 1.35 (d, 6H). $^{13}$C-NMR (CDCl$_3$) δ 190.2, 160.8, 140.6, 129.0, 127.2, 117.2, 114.6, 107.5, 56.7. Mass Spectrum m/e (M+1) 327. Anal. Calcd. For C$_{20}$H$_{22}$O$_4$.0.5 H$_2$O: C, 73.59; H, 6.80. Found C, 71.62; H, 6.91.

Example 14

(E)-1-(4-propoxyphenyl)-3-(3-methoxyphenyl)prop-1-en-3-one (DMU-417)

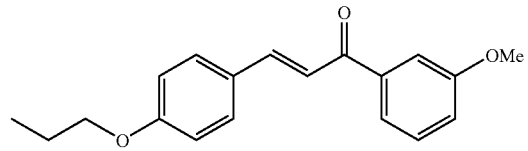

To a stirred solution of 4-propoxybenzaldehyde (1 g, 6.09 mmol) and 3-methoxyacetophenone (0.91 g, 6.09 mmol) in methanol (30 ml) was added 50% w/v solution of aqueous sodium hydroxide (9.7 ml, 0.122 mol). The reaction mixture was stirred at room temperature for 24 h. A precipitate was isolated by filtration, washed with cold methanol and subsequently recrystallised from methanol to afford 0.38 g (21%) of pale yellow crystals. $^1$H-NMR δ (CDCl$_3$), 1.6 (t, 3H), 1.85 (m, 2H), 3.9 (s, 2H), 3.95 (t, 2H), 6.9 (d, 2H), 7.1 (1H), 7.38 (m, 2H), 7.55 (m, 4H), 7.8 (d, 1H). $^{13}$C-NMR (CDCl$_3$) δ 190.3, 161.3, 159.9, 139.9, 127.4, 69.6, 22.5. Mass Spectrum m/e (M+1) 297. Anal. Calcd. for C$_{19}$H$_{20}$O$_3$: C, 77.00; H, 6.80. Found C, 76.86; H, 6.94.

Example 15

(E)-1-(4-propoxyphenyl)-3-(2,4-dimethoxyphenyl)prop-1-en-3-one (DMU-408)

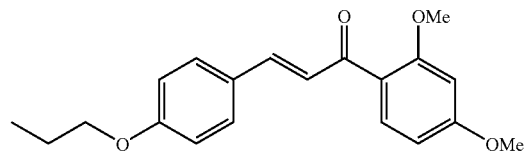

To a stirred solution of 4-propoxybenzaldehyde (1.0 g, 6.1 mmol) and 2,'4'-dimethoxyacetophenone (1.1 g, 6.1 mmol) in methanol (30 ml) was added 50% w/v solution of aqueous sodium hydroxide (9.7 ml, 0.122 mol). The reaction mixture was stirred at room temperature for 2 h. A precipitate was isolated by filtration and subsequently recrystallised from methanol to afford 0.31 g (16%) of pale yellow crystals. $^1$H-NMR (CDCl$_3$) δ 1.0 (t, 3H), 1.7 (m, 2H), 3.85 (s, 3H), 3.9 (s, 3H), 3.9 (t, 2H), 6.5 (dd, 2H), 6.85 (d, 2H), 7.3 (d, 1H), 7.6 (d, 2H), 7.5 (d, 2H). $^{13}$C-NMR (CDCl$_3$) δ 190.6, 163.9, 160.7, 160.2, 127.9, 122.5, 69.6, 22.5. Mass Spectrum m/e (M+1) 327. Anal. Calcd. for C$_{20}$H$_{22}$O$_4$: C, 73.62; H, 6.75. Found C, 73.48; H, 6.81.

Example 16

(E)-1-(4-propoxyphenyl)-3-(2,3,4-trimethoxyphenyl)prop-1-en-3-one (DMU-420)

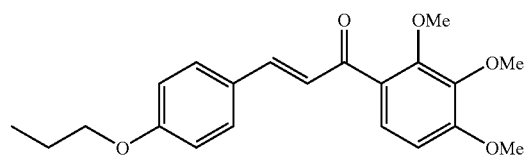

To a stirred solution of 4-propoxybenzaldehyde (0.781 g, 4.8 mmol) and 2,3,4-trimethoxyacetophenone (1.0 g, 4.8 mmol) in methanol (30 ml) was added a 50% w/v solution of aqueous NaOH (7.60 ml, 0.096 mol). The reaction mixture was stirred at room temperature for 24 h. A pale yellow precipitate was isolated and dried under vacuum over night. 1.693 g (86%) of a pale yellow powder was isolated. $^1$H-NMR (CDCl$_3$) δ 7.60 (d, 1H), 7.5 (m, 1H), 4.4 (d, 1H), 7.3 (d, 1H), 6.8 (m, 1H), 6.7 (d, 1H), 3.9 (t, 2H), 3.9 (s, 3H), 3.9 (s, 3H), 3.9 (s, 3H), 1.75 (m, 2H), 1.0 (t, 3H). $^{13}$C-NMR (CDCl$_3$) δ 191.0. Mass Spectrum m/e (M+1) 357. Anal. Calcd. for $C_{21}H_{24}O_5 \cdot H_2O$: C, 67.44; H, 7.01. Found: C, 67.49; H, 6.93.

Example 17

(E)-1-(4-propoxyphenyl)-3-(2,5-dimethoxyphenyl) prop-1-en-3-one (DMU-424)

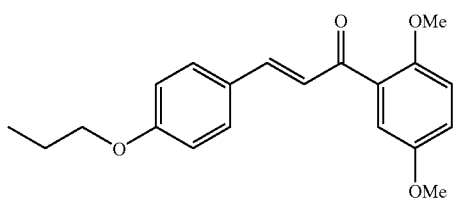

To a stirred solution of 4-propoxybenzaldehyde (1 g, 6.1 mmol) and 2',5'-dimethoxyacetophenone (1.1 g, 6.1 mmol) in methanol (15 ml) was added 50% w/v solution of aqueous sodium hydroxide (9.7 ml, 0.122 mol). The reaction mixture was stirred at room temperature for 18 h. A precipitate was isolated by filtration and subsequently recrystallised from ethanol to afford 0.97 g (49%) of pale yellow crystals. $^1$H-NMR (CDCl$_3$) δ 1.0 (t, 3H), 1.8 (m, 2H), 3.7 (s, 3H), 3.8 (s, 3H), 3.9 (t, 2H), 6.9 (m, 3H), 6.9 (d, 1H) 7.15 (d, 1H), 7.25 (d, 1H), 7.5 (m, 3H), $^{13}$C-NMR (CDCl$_3$) δ 192.59, 160.86, 161.11, 153.59, 152.34, 130.07, 127.56, 22.47. Mass Spectrum m/e (M+1) 327. Anal. Calcd. for $C_{20}H_{2}O_4$: C, 73.62; H, 6.75. Found C, 73.55; H, 6.88.

Example 18

(E)-1-(4-propoxyphenyl)-2-methyl-3-(3,5-dimethoxyphenyl)prop-1-en-3-one (DMU-432)

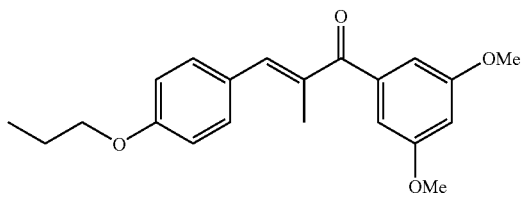

3,5-Dimethoxybenzaldehyde (4.0 g, 0.024 mol), in dry tetrahydrofuran (100 ml), was added over 15 min to ethylmagnesium bromide (28.9 ml (1.0 M solution in tetrahydrofuran) 0.029 mmol) in dry tetrahydrofuran (50 ml) at 0° C., under nitrogen. After refluxing the mixture for 18 h a grey solution was obtained. The reaction was then quenched by adding ice and 1 M hydrochloric acid (100 ml) dropwise and the aqueous phase was extracted with ether (3×100 ml), the combined organic layers were dried over anhydrous magnesium sulphate and reduced in vacuo. Purification by column chromatography (SiO$_2$, petroleum:ether (40:60 v/v) with an increasing gradient of ethyl acetate (0–20%)) gave 3.53 g (74.8%) of the alcohol as a yellow oil.

To a stirred solution of dimethylsulfoxide (2.86 ml, 0.040 mol) in dry dichloromethane (30 ml) at −78° C. was added, over 15 min, oxalyl chloride (1.75 ml, 0.020 mol) under nitrogen. The solution was stirred for 15 min at −78° C. until the evolution of gas stopped, then a solution of the alcohol (3.5 g, 0.018 mol) in dichloromethane (30 ml) was added over 15 min. The mixture was stirred at −78° C. for a further 30 min before triethylamine (12.47 ml, 0.09 mol) was added over 10 min, this was stirred for a further 5 min at −78° C. and then allowed to warm up to room temperature and left for 2 h. The mixture was then diluted with dichloromethane (30 ml) and the organic layer was sequentially washed with 1 M hydrochloric acid (2×50 ml), water (2×50 ml), dried over magnesium sulphate and reduced in vacuo. Purification by column chromatography (SiO$_2$, petroleum:ether (40:60 v/v) with an increasing gradient of ethyl acetate) gave 2.85 g (81%) of the ketone as a yellow solid.

A mixture of the ketone (1.55 g, 7.9 mmol), 4-propoxybenzaldehyde (1.24 ml, 7.8 mmol), piperidine (1.76 ml, 17.8 mmol) and glacial acetic acid (0.883 ml, 15 mmol) in dry ethanol (100 ml) were heated under reflux and water was removed from the reaction by soxhlet extraction over 4A molecular sieves for 50 h. The solvent was removed in vacuo and the residue was purified by column chromatography (SiO$_2$, petroleum:ether (40:60 v/v) with an increasing gradient of ethyl acetate) to give 0.20 g (7%) of a yellow oil. $^1$H-NMR (CDCl$_3$) δ 7.3 (d, 2H), 7.1 (s, 1H), 6.8 (d, 2H), 6.7 (d, 2H), 6.5 (t, 1H), 3.8 (t, 2H), 3.7 (s, 6H), 2.2 (t, 3H), 1.7 (q, 2H), 0.9 (t, 3H). $^{13}$C-NMR (CDCl$_3$) δ 198.9, 160.5, 159.6, 142.9, 140.9, 134.4, 131.6, 128.0, 126.9, 114.5, 107.2, 103.5, 69.5, 55.4, 42.9, 38.7, 31.6, 22.5, 19.7, 14.3, 10.5.

(Comparative: Tertiary Alkyl) Example 1

(E)-1-(4-tertbutoxyphenyl)-3-(3,5-dimethoxyphenyl) prop-1-en-3-one (DMU-402)

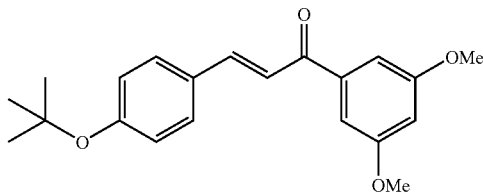

To a stirred solution of 3,5-dimethoxyacetophenone (1.0 g, 5.55 mmol) and 4-t-butoxybenzaldehyde (0.99 g, 5.55 mmol) in methanol (30 ml) was added a 50% w/v solution of aqueous sodium hydroxide (8.8 ml, 0.11 mol). The reaction mixture was stirred for 4 h at room temperature; no precipitate was observed. The product was extracted with ethyl acetate (3×50 ml), the combined organic layers were dried over anhydrous magnesium sulphate and reduced in vacuo. Purification by column chromatography (SiO$_2$, petroleum:ether (40:60 v/v) with an increasing gradient of ethyl acetate) afforded 1.19 g (63%) of a yellow oil. $^1$H-NMR (CDCl$_3$) δ 7.7 (d, 1H), 7.5 (m, 2H), 7.36 (d, 1H), 7.1 (d, 2H), 7.0 (m, 2H), 6.6 (t, 1H), 3.8 (s, 6H), 1.4 (s, 9H). $^{13}$C-NMR (CDCl$_3$) δ 190.0, 160.9, 158.2, 140.4, 130.7, 129.5, 128.2, 124.9, 122.3, 119.4, 107.5, 104.9, 79.4, 56.7, 54.4, 29.9, 27.9. Mass Spectrum m/e (M+1) 341. Anal. Calcd. for C$_{21}$H$_{24}$O$_4$.0.5 H$_2$O: C, 74.09; H, 7.10. Found C, 72.18; H, 7.21.

Biological Activity

TCDD-Induced MCF-7 Cell Line Versus MCF-7 Cell Line Cytotoxicity Assay

CYP1A1 and CYP1B1 enzyme activity is induced by TCDD (tetrachlorodibenzodioxin (Dioxin)) in breast tumour MCF-7 cells (see, e.g., Sutter et al., 1994). CYP1B1 is expressed in a variety of human tumours, and can be inducible by TCDD in numerous cell types including breast, liver, lung, and kidney (see, e.g., Murray et al., 1997). CYP1B1 is known to catalyse estradiol 4-hydroxylation metabolism. In untreated culture, the constitutive rate of estradiol E$_2$ metabolism in MCF-7 cells is minimal. However, treatment with TCDD causes a marked increase in the rate of E$_2$ metabolism (see, e.g., Spink et al., 1994). Thus MCF-7 cells in culture that are non-induced are metabolically analogous to normal cells that do not express CYP1B1, whilst TCDD-induced MCF-7 cells express the CYP1B1 enzyme as is present in fresh human tumours. Therefore the cytotoxicity of compounds in non-induced MCF-7 cells correlates to the cytotoxicity of compounds against normal cells, whilst the cytotoxicity of compounds against TCDD-induced MCF-7 cells correlates to the cytotoxicity of compounds against real tumours that express CYP1B1. In this assay, a tumour selectivity factor greater than 1 (and preferably greater than 1.5) is highly significant and demonstrates that the compound has tumour selective cytotoxic activity.

The non-induced MCF-7 cell line is analogous enzymatically to normal cells that do not express catalytically active CYP1 family enzymes. The cytotoxicity of compounds in non-induced MCF-7 cells correlates to the cytotoxicity of compounds against normal cells, whilst the cytotoxicity of compounds against TCDD-induced MCF-7 cells correlates to the cytotoxicity of compounds against real tumours that express CYP1B1.

Cells were maintained in RPMI 1640 with Glutamax 1 (Life Technologies) with 10% (v/v) heat inactivated foetal calf serum (Hybrimax. Sigma), at 37° C., 5% CO$_2$/95% air with 100% humidity and passaged using trypsin/EDTA. 1×10$^3$ cells were plated out in 100 μl medium per well of 96-well flat-bottomed plates (Fisher). After 4 hours to allow adherance, 100 μl of medium containing TCDD (British Greyhound Chromatography; 10 μM stock in DMSO (dimethylsulfoxide)) or medium with 0.2% (v/v) DMSO as control was added to each well to give a final concentration of 10 nM TCDD, 0.1% (v/v) DMSO, for 24 hours to allow maximal CYP expression. The medium was then carefully aspirated and 100 μl fresh medium added. Within 30 minutes test compound was added in quadruplicate in 100 μl medium (with or without inhibitors) at double the final concentration from 100 mM stock in DMSO to give a final concentration of not more than 0.1% (v/v) DMSO, or DMSO solvent alone at 0.1% (v/v) as control. The cells were then allowed to grow on for 96 hours to give 80–90% confluence in the control wells. 50 μl MTT (Thiazol blue, Sigma) at 2 mg/ml in Dulbecco's phosphate buffered saline-A, was then added to each well for 3 hours. All medium was aspirated, then the formazan product generated by viable cells was solubilized with 150 μl DMSO. Plates were vortexed and the absorbance at 540 nm determined using a plate reader. Results were expressed as the percentage of 100% (control) proliferation and the IC50 calculated using the line of best fit for a sigmoidal dose response curve with variable slope using Graphpad Prizm software. All determinations were carried out in at least triplicate.

The selectivity differential factor (TSDF) is calculated by dividing the IC50 obtained from the MCF-10A data by the IC50 obtained from the MDA468 data. A selectivity factor greater than 1 (and preferably greater than 1.5) is highly significant and demonstrates that the compound has tumour selective cytotoxic activity.

The results of this assay are summarised in the table below. Compound DMU-1.75 is 30-fold more toxic to "tumour" cells than to "normal" cells. Compound DMU-186 is 46-fold more toxic. Compound DMU-191 is 24-fold more toxic. Compound DMU-103 (see compound 1 in Ikeda Shunichi et al., 1996) is 2-fold more toxic to normal cells than to cancer cells.

TABLE 1

| | Cytotoxicity | | |
|---|---|---|---|
| Compound | MCF-7 Cells IC50 (μM) | TCDD-induced MCF-7 Cells IC50 (μM) | Tumour Selectivity Differential Factor |
| DMU-174 | 2.0 | 0.6 | 3 |
| DMU-175 | 15.0 | 0.5 | 30 |
| DMU-176 | 20.0 | 1.1 | 18 |
| DMU-185 | 8.0 | 0.66 | 12 |
| DMU-186 | 30.0 | 0.65 | 46 |
| DMU-190 | 0.75 | 0.39 | 2 |
| DMU-191 | 10.0 | 0.42 | 24 |
| DMU-192 | 20.0 | 1.6 | 12 |
| DMU-188 | 4.5 | 0.6 | 8 |
| DMU-189 | 8.3 | 2.5 | 3 |
| DMU-401 | 6.8 | 0.8 | 9 |
| DMU-417 | 28 | 10 | 3 |
| DMU-408 | 10 | 1.3 | 8 |
| DMU-420 | 20 | 3.7 | 5 |
| DMU-424 | 12 | 2 | 6 |
| DMU-432 | 0.7 | 0.08 | 9 |
| DMU-103 | 0.04 | 0.08 | 0.5 |
| DMU-402 | 6.2 | 6.2 | 1 |

FIG. 1 is a graph of cell survivial (%) versus concentration (μM) of compound DMU-175, for (A) the TCDD-induced MCF-7 cell line (■) and (B) the MCF-7 cell line (▼).

This graph shows that compound DMU-175 has an IC50 of 15 μM in un-induced MCF-7 cells, but has an IC50 of 0.54 μM in TCDD-induced MCF-7 cells. This illustrates a surprising and unexpected 28-fold increase in the cytotoxic activity of DMU-175 by the induction of CYP1B1. Consequently, DMU-175 has a large therapeutic window; is active at much lower doses; and will specifically target the tumour cells that express CYP1B1, whilst normal cells will be preferentially spared.

MDA468 Tumour Cell Line Versus MCF-10A Normal Cell Line Assay

This cell culture based assay is performed using the two cell lines MDA-468 and MCF-10A. The MDA468 cell line is an advanced breast cancer cell line, whilst the MCF-10A cell line is a normal breast cell line.

This assay was performed using the two cell lines MDA-468 and MCF-10A according to the procedure described above for the MCF-7 assay, but without the addition of TCDD.

The tumour selectivity differential factor (TSDF) is calculated by dividing the IC50 obtained from the MCF-10A data by the IC50 obtained from the MDA-468 data. In this assay, a tumour selectivity factor greater than 1 (and preferably greater than 1.5) is highly significant and demonstrates that the compound has tumour selective cytotoxic activity.

The results of this assay on Compound DMU-175, together with the clinically used anticancer agents tamoxifen, methotrexate, and doxorubicin (adriamycin) for comparison, are summarised in the table below. Surprisingly compound DMU-175 is 11-fold more toxic to cancer cells than to normal cells. In contrast, the clinically used anticancer agent Doxorubicin is actually found to be 10-fold more toxic to normal cells than to cancer cells.

TABLE 2

| Compound | Cytotoxicity | | |
|---|---|---|---|
| | MDA-468 (Breast Tumour) IC50 (uM) | MCF-10A (Normal Breast) IC50 (uM) | Tumour Selectivity Differential Factor |
| DMU-175 | 1.4 | 16 | 11 |
| Tamoxifen | 4.0 | 6.3 | 1.6 |
| Methotrexate | 0.04 | 0.06 | 1.5 |
| Doxorubicin | 0.003 | 0.0003 | 0.1 |

Figure 2:
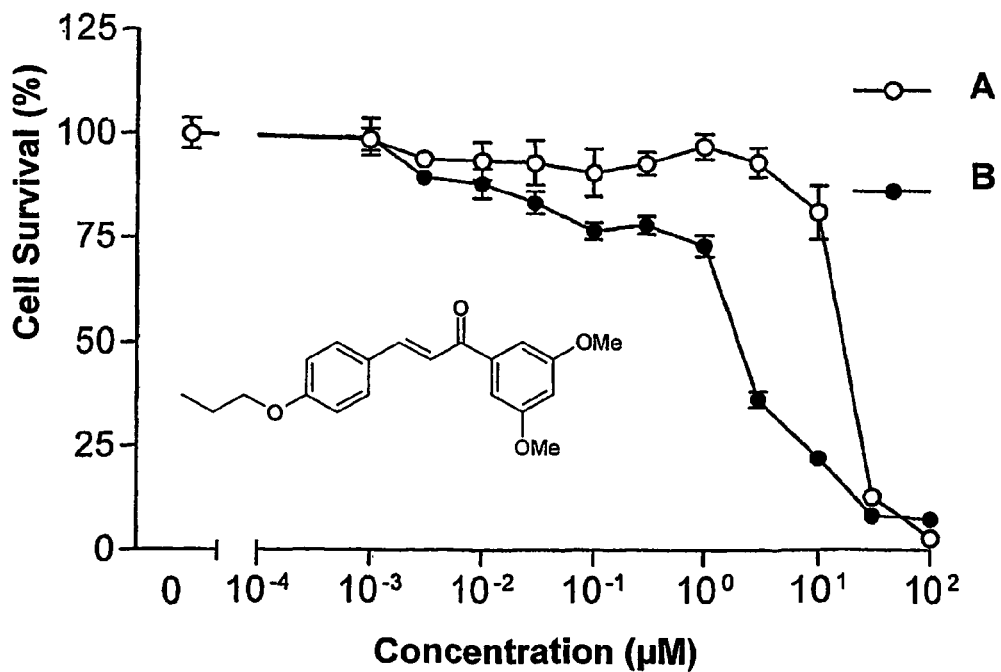
FIG. 2 is a graph of cell survivial (%) versus concentration (μM) of compound DMU-175, for (A) the normal breast cell line MCF-10A (○), and (B) the advanced breast cancer cell line MDA-468 (●).

FIG. 2 is a graph of cell survivial (%) versus concentration (μM) of compound DMU-175, for (A) the normal breast cell line MCF-10A (○), and (B) the advanced breast cancer cell line MDA468 (●).

This graph shows that compound DMU-175 shows a low toxicity IC50 value of 16 μM against the normal cell line, but a highly potent IC50 value of 1.4 μM against the advanced tumour cell line. This illustrates a surprising and unexpected 11-fold tumour selectivity in the cytotoxic activity of DMU-175.

Splenocyte Anti-Proliferation Assay

The splenocyte anti-proliferation assay has been developed to identify compounds that have useful anti-inflammatory properties for the treatment of auto-inflammatory diseases such as rheumatoid arthritis. See, for example, Yamashita et al., 1994. This well known assay is described in detail in, for example, Mosmann, 1983. In this assay, splenocyte proliferation is stimulated by the inflammatory response inducer conconavilin A (Con A). Cell proliferation is monitored by detecting radiation (counts per minute, cpm) from a radio label (tritiated thymidine) which is incorporated only into proliferating cells.

For example, compounds may be assayed as a solution in dimethylsulfoxide (DMSO) as solvent. A solvent control may also be tested for comparison. Other controls may be used. Compounds that exhibit anti-inflammatory effects at a concentration of less than 10 μM are considered to be useful therapeutic agents.

The compounds of the present invention also show growth down-regulatory effects on splenocytes. Since splenocytes are involved in inflammation, these compounds are also useful as anti-inflammatory agents.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Barrie, S. E., et al., 1989, "Inhibition of 17-hydroxylase/C17–C20 Lyase by Bifluranol and Its Analogues," *J. Steroid Biochem.*, Vol. 33, No. 6, pp. 1191–1195.

Berryman et al., 1995, published international (PCT) patent application number WO 95/05376, published 23 Feb. 1995.

Berryman et al., 1997, U.S. Pat. No. 5,691,373, granted 25 Nov. 1997.

Carmichael, J., et al., 1987, "Evaluation of a Tetrazolium-based Semiautomated Colorimetric Assay: Assessment of Chemosensitivity Testing," *Cancer Research*, Vol. 47, p. 936–942.

Cushman et al., 1995, U.S. Pat. No. 5,430,062, granted 04 Jul. 1995.

Ducki, S., et al., 1998, "Potent Antimitotic and Cell growth Inhibitory Properties of Substituted Chalcones," *BioMed. Chem. Left.*, Vol. 8, pp. 1051–1056.

Eda Shoei et al., 1986, Japanese patent publication number JP-61-076433A (application number JP-59-199262) published 18 Apr. 1986.

Hall et al., 1981, U.S. Pat. No. 4,279,930, granted 21 Jul. 1981.

Ikeda Shunichi et al., 1996, Japanese patent publication number JP-08-188546A (application number JP-07-000002) published 23 Jul. 1996.

Kharazmi et al., 1999, published international (PCT) patent application number WO 99/00114, published 7 Jan. 1999.

Melvin et al., 1997, published international (PCT) patent application number WO 97/12246, published 3 Apr. 1997.

Mosmann, T., 1983, "Rapid Colorimetric Assay for Cellular Growth and Survival: Application to Proliferation and Cytotoxicity Assays," *Journal of Immunological Methods*, Vol. 65, pp. 55–63.

Murray, G. I., et al., 1997, "Tumour-specific Expression of Cytochrome P450 CYP1B1," *Cancer Research*, Vol. 57, pp. 3026–3031.

Pettit, G. R., et al., 1995, "Antineoplastic agents 322. Synthesis of Combretastatin A-4 Prodrugs," *Anticancer Drug Design*, Vol. 10, pp. 299–309.

Potter et al., 1999, published international (PCT) patent application number WO 99/40056, published 12 Aug. 1999.

Potter et al., 2001 a, U.S. Pat. No. 6,214,886, granted 10 Apr. 2001.

Potter et al., 2001b, published international (PCT) patent application number WO 01/72680, published 04 Oct. 2001.

Spink, D. C., et al., 1994, "The Effects of 2,3,7,8-Tetrachlorodibenzo-p-dioxin on Estrogen Metabolism in MCF-7 Breast Cancer Cells: Evidence for Induction of a Novel 17β-Estradiol 4-hydroxylase," *J. Steroid Biochem. Mol. Biol.*, Vol. 51, No. 5/6, pp. 251–258.

Sutter, T. R., et al, 1994, "Complete cDNA sequence of a human dioxin-inducible mRNA identifies a new gene subfamily of cytochrome P450 that maps onto chromosome 2," *J. Biol. Chem.*, Vol. 269, No. 18, pp. 13092–13099.

Yamashita, D. S., et al, 1994, "Design, Synthesis and Evaluation of Dual Domain FKBP Ligands," *Bioorg. Med. Chem. Left.*, Vol. 4, No. 2, pp. 325–328.

What is claimed is:
1. A compound of the following formula:

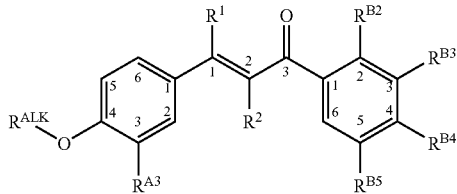

wherein:
  $R^{ALK}$ is primary or secondary aliphatic saturated $C_{2-6}$alkyl;
  two of $R^{B2}$, $R^{B3}$, $R^{B4}$, and $R^{B5}$ are —OMe;
  and the others are independently —H or —OH;
  or:
  three of $R^{B2}$, $R^{B3}$, $R^{B4}$, and $R^{B5}$ are —OMe;
  and the other is independently —H or —OH;
  each of $R^1$ and $R^2$ is independently:
    —H,
    optionally substituted $C_{1-4}$alkyl, or
    optionally substituted $C_{5-20}$aryl;
  $R^{A3}$ is —H, —OH, —OC(=O)$R^E$, —OS(=O)$_2$OH, or —OP(=O)(OH)$_2$;
  $R^E$ is:
    —H,
    optionally substituted $C_{1-6}$alkyl,
    optionally substituted $C_{3-20}$heterocyclyl, or
    optionally substituted $C_{5-20}$aryl;
  and pharmaceutically acceptable salt, solvates, amides, esters, and ethers thereof.

2. A compound according to claim 1, wherein $R^{ALK}$ is selected from:

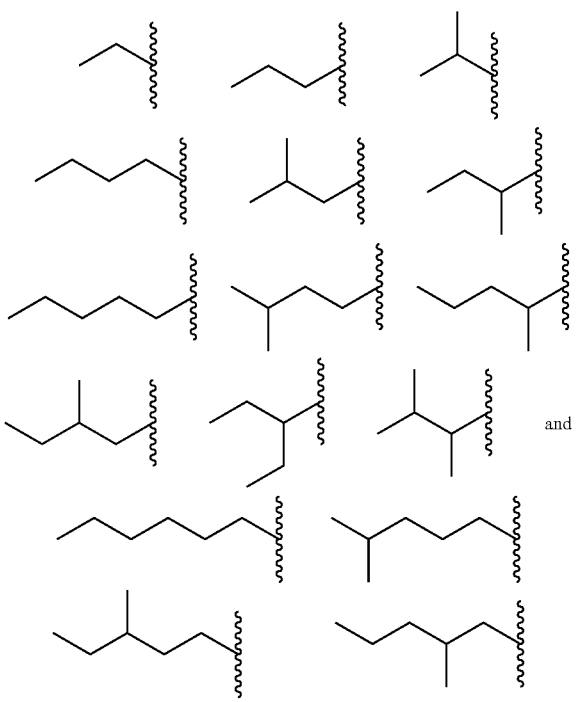

and

-continued

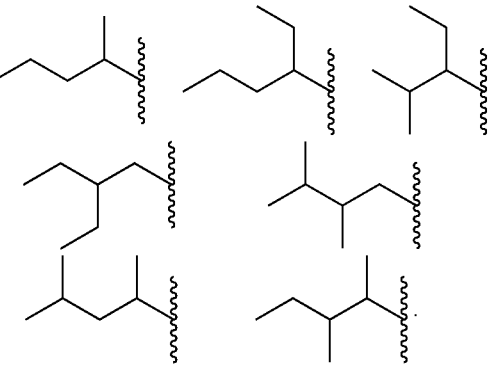

3. A compound according to claim 1, wherein $R^{ALK}$ is selected from:
  -Et, -nPr, -iPr, -nBu, -iBu, -sBu, -nPe, and -nHex.

4. A compound according to claim 1, wherein $R^{ALK}$ is selected from:
  -nPr, -nBu, -nPe, and -nHex.

5. A compound according to claim 1, wherein:
  each of $R^1$ and $R^2$ is independently —H or -Me.

6. A compound according to claim 1, wherein:
  $R^1$ and $R^2$ are both —H.

7. A compound according to claim 6, wherein:
  two of $R^{B2}$, $R^{B3}$, $R^{B4}$, and $R^{B5}$ is —OMe; and
  the others are independently —H or —OH.

8. A compound according to claim 6, wherein:
  two of $R^{B2}$, $R^{B3}$, $R^{B4}$, and $R^{B5}$ is —OMe;
  the others are independently —H or —OH; and
  the two —OMe groups are not adjacent to each other.

9. A compound according to claim 6, wherein:
  two of $R^{B2}$, $R^{B3}$, $R^{B4}$, and $R^{B5}$ is —OMe;
  one of the others is —OH; and
  the last is —H.

10. A compound according to claim 6, wherein:
  two of $R^{B2}$, $R^{B3}$, $R^{B4}$, and $R^{B5}$ is —OMe;
  one of the others is —OH;
  the last is —H; and
  the two —OMe groups are not adjacent to each other.

11. A compound according to claim 6, wherein:
  three of $R^{B2}$ $R^{B3}$ $R^{B4}$ and $R^{B5}$ is —OMe; and
  the others are independently —H or —OH.

12. A compound according to claim 6, wherein:
  two of $R^{B2}$, $R^{B3}$, $R^{B4}$, and $R^{B5}$ is —OMe; and
  the others are —H.

13. A compound according to claim 6, wherein:
  two of $R^{B2}$, $R^{B3}$, $R^{B4}$, and $R^{B5}$ is —OMe;
  the others are —H; and
  the two —OMe groups are not adjacent to each other.

14. A compound according to claim 6, wherein:
  three of $R^{B2}$, $R^{B3}$, $R^{B4}$, and $R^{B5}$ is —OMe; and
  the other is —H.

15. A compound according to claim 1, selected from compounds of the following formulae, and pharmaceutically acceptable salts, solvates, amides, esters, and ethers thereof:

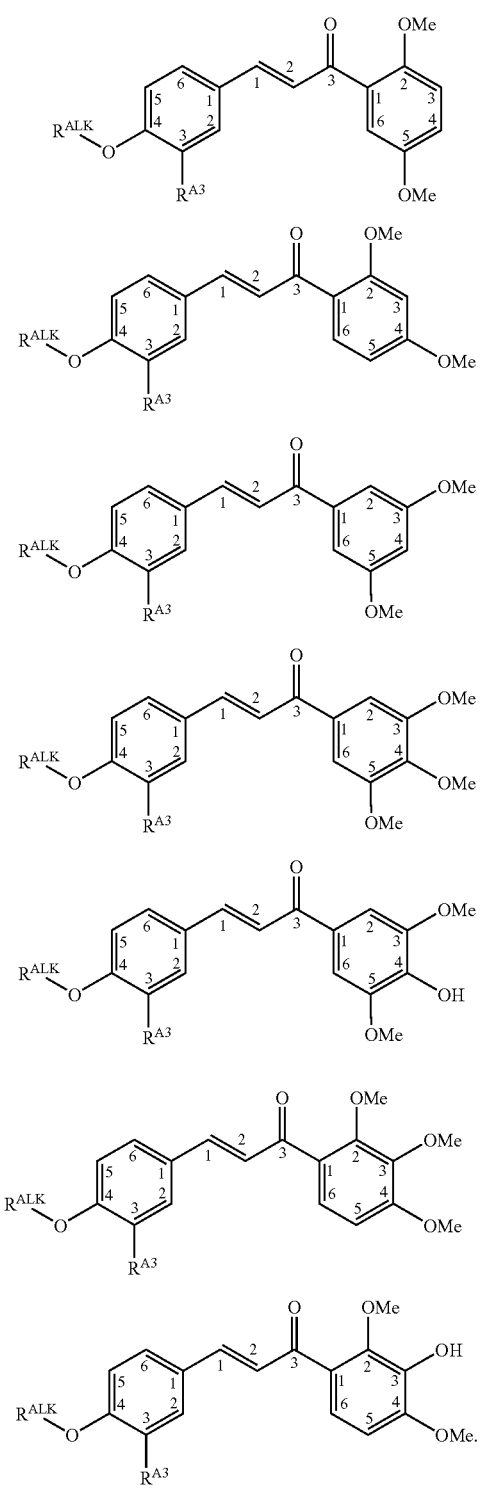

16. A compound according to claim 1, wherein:
$R^E$ is —CH$_3$, —CH$_2$CH$_3$, —C(CH$_3$)$_3$, or -Ph.

17. A compound according to claim 1, wherein $R^{A3}$ is —H.

18. A compound according to claim 2, wherein $R^{A3}$ is —H.

19. A compound according to claim 3, wherein $R^{A3}$ is —H.

20. A compound according to claim 4, wherein $R^{A3}$ is —H.

21. A compound according to claim 5, wherein $R^{A3}$ is —H.

22. A compound according to claim 6, wherein $R^{A3}$ is —H.

23. A compound according to claim 7, wherein $R^{A3}$ is —H.

24. A compound according to claim 8, wherein $R^{A3}$ is —H.

25. A compound according to claim 9, wherein $R^{A3}$ is —H.

26. A compound according to claim 10, wherein $R^{A3}$ is —H.

27. A compound according to claim 11, wherein $R^{A3}$ is —H.

28. A compound according to claim 12, wherein $R^{A3}$ is —H.

29. A compound according to claim 13, wherein $R^{A3}$ is —H.

30. A compound according to claim 14, wherein $R^{A3}$ is —H.

31. A compound according to claim 15, wherein $R^{A3}$ is —H.

32. A compound according to claim 1, wherein $R^{A3}$ is —OH.

33. A compound according to claim 2, wherein $R^{A3}$ is —OH.

34. A compound according to claim 3, wherein $R^{A3}$ is —OH.

35. A compound according to claim 4, wherein $R^{A3}$ is —OH.

36. A compound according to claim 5, wherein $R^{A3}$ is —OH.

37. A compound according to claim 6, wherein $R^{A3}$ is —OH.

38. A compound according to claim 7, wherein $R^{A3}$ is —OH.

39. A compound according to claim 8, wherein $R^{A3}$ is —OH.

40. A compound according to claim 9, wherein $R^{A3}$ is —OH.

41. A compound according to claim 10, wherein $R^{A3}$ is —OH.

42. A compound according to claim 11, wherein $R^{A3}$ is —OH.

43. A compound according to claim 12, wherein $R^{A3}$ is —OH.

44. A compound according to claim 13, wherein $R^{A3}$ is —OH.

45. A compound according to claim 14, wherein $R^{A3}$ is —OH.

46. A compound according to claim 15, wherein $R^{A3}$ is —OH.

47. A compound according to claim 1 selected from compounds of the following formulae, and pharmaceutically acceptable salts, solvates, amides, esters, and ethers thereof:

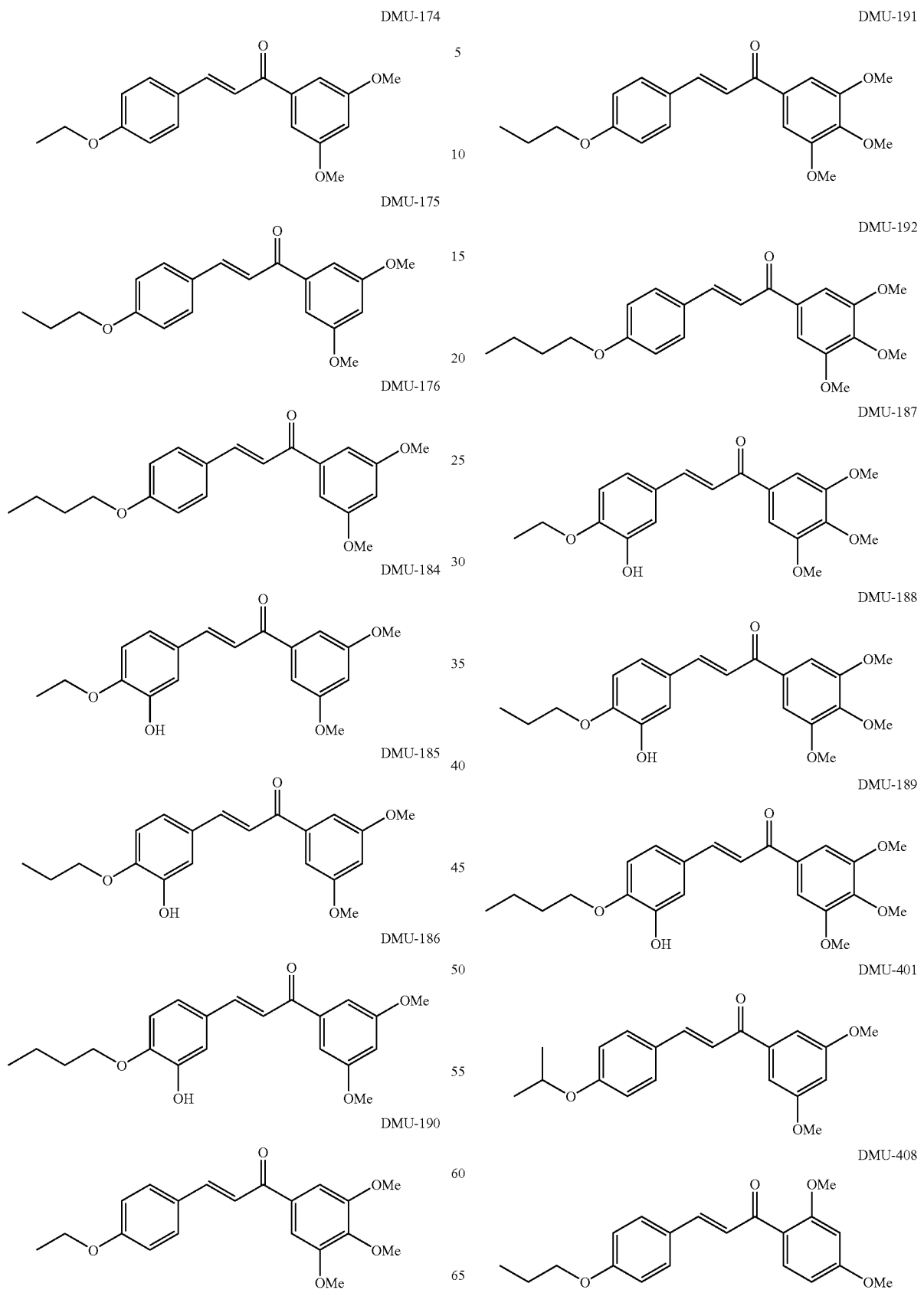

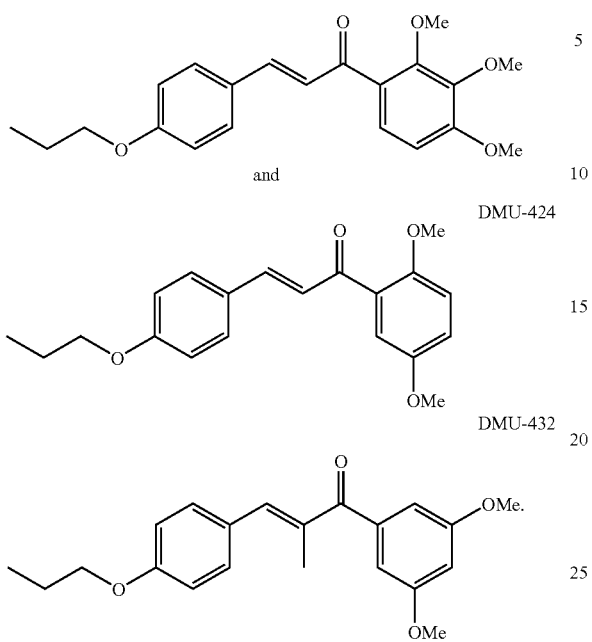

DMU-420 and

DMU-424

DMU-432

48. A composition comprising a compound according to claim 1 and a pharmaceutically acceptable carrier.

49. A method of treating a proliferative condition in a patient comprising administering to said patient a therapeutically-effective amount of a compound according to claim 1.

50. A method according to claim 49, wherein the proliferative condition is a solid tumour.

51. A method according to claim 49, wherein the proliferative condition is a solid tumour, and is a cancer of the lung, colon, breast, ovarian, prostate, liver, pancreas, brain, or skin.

52. A method according to claim 49, wherein the proliferative condition is a solid tumour, and is a cancer of the breast.

53. A method according to claim 49, which is a method of prophylactically treating said proliferative condition.

54. A method of treating an inflammatory condition in a patient comprising administering to said patient a therapeutically-effective amount of a compound according to claim 1.

55. A method according to claim 54, wherein the inflammatory condition is rheumatoid arthritis, rheumatic fever, osteoarthritis, inflammatory bowel disease, psoriasis, or bronchial asthma.

56. A method of diagnosis of a patient for the presence of tumour cells expressing the CYP1B1 enzyme, comprising:
  (a) administering to the patient a compound as defined below, wherein $R^{43}$ is —H;
  (b) determining the amount of corresponding hydroxylated metabolite, wherein $R^{43}$ is —OH, which is subsequently produced; and,
  (c) correlating the amount with the presence or absence of the tumour cells in the patient;
wherein the compound is selected from compounds of the following formula:

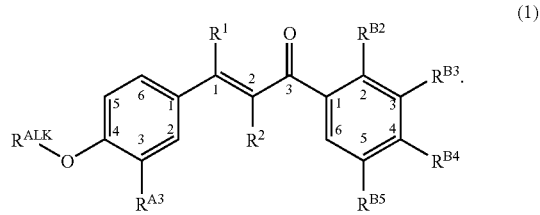

(1)

wherein:
$R^{ALK}$ is primary or secondary aliphatic saturated $C_{2-6}$alkyl;
two of $R^{B2}$, $R^{B3}$, $R^{B4}$, and $R^{B5}$ are —OMe;
and the others are independently —H or —OH;
or:
three of $R^{B2}$, $R^{B3}$, $R^{B4}$, and $R^{B5}$ are —OMe;
and the other is independently —H or —OH;
each of $R^1$ and $R^2$ is independently:
  —H
  optionally substituted $C_{1-4}$alkyl, or
  optionally substituted $C_{5-20}$aryl;
$R^{43}$ is —H;
$R^E$ is:
  —H
  optionally substituted $C_{1-6}$alkyl,
  optionally substituted $C_{3-20}$heterocyclyl, or
  optionally substituted $C_{5-20}$aryl;
and pharmaceutically acceptable salts, solvates, amides, esters, and ethers thereof.

* * * * *